United States Patent [19]

Durante et al.

[11] Patent Number: 5,439,859
[45] Date of Patent: Aug. 8, 1995

[54] PROCESS AND CATALYST FOR DEHYDROGENATION OF ORGANIC COMPOUNDS

[75] Inventors: Vincent A. Durante, West Chester; Daniel E. Resasco, Media, both of Pa.; Darrell W. Walker, Visalia, Calif.; Gary L. Haller, Hamden, Conn.; Eugene L. Coggins, Malvern, Pa.

[73] Assignee: Sun Company, Inc. (R&M), Philadelphia, Pa.

[21] Appl. No.: 874,499

[22] Filed: Apr. 27, 1992

[51] Int. Cl.⁶ .................. B01J 29/064; B01J 29/072
[52] U.S. Cl. ....................... 502/66; 502/74; 502/242; 502/327; 502/259; 502/337; 502/222; 502/253; 502/237; 502/216; 502/168
[58] Field of Search .......... 502/66, 74, 242, 327, 502/259, 337, 222, 253, 257, 216, 168

[56] References Cited

U.S. PATENT DOCUMENTS

| | | | |
|---|---|---|---|
| 3,580,970 | 5/1971 | Swift | 502/242 |
| 3,637,529 | 1/1972 | Van Beek et al. | 502/337 |
| 3,780,129 | 12/1973 | Friedrich | 502/242 |
| 3,799,983 | 3/1974 | Corr et al. | 502/259 |
| 3,960,773 | 6/1976 | Bertus et al. | 502/242 |
| 3,966,895 | 6/1976 | Wilhelm | 260/668 |
| 4,251,394 | 2/1981 | Carter et al. | 252/452 |
| 4,252,680 | 2/1981 | Walker et al. | 252/435 |
| 4,435,607 | 3/1984 | Imai | 585/443 |
| 4,517,306 | 5/1985 | Buss | 502/66 |
| 4,601,996 | 7/1986 | Miller | 502/259 |
| 4,727,216 | 2/1988 | Miller | 585/660 |
| 4,746,643 | 5/1988 | Buonomo et al. | 502/243 |
| 4,788,371 | 11/1988 | Imai et al. | 585/443 |
| 4,806,624 | 2/1989 | Herber et al. | 585/440 |
| 4,902,849 | 2/1990 | McKay et al. | 585/660 |

FOREIGN PATENT DOCUMENTS

416710A 3/1991 European Pat. Off. ........ B01J 8/02

Primary Examiner—Asok Pal
Attorney, Agent, or Firm—Q. Todd Dickinson; Donald R. Johnson

[57] ABSTRACT

Alkanes are dehydrogenated by passage through alternating dehydrogenation zones and selective oxidation zone(s), in which latter zone(s) hydrogen produced in the preceding endothermic dehydrogenation reaction is selectively oxidized to generate heat for the succeeding dehydrogenation reaction. New catalyst compositions are prepared comprising reduced and sulfided nickel crystallites on siliceous supports which have been treated with chromium compounds and oxidized to provide surface-anchored chromyl species. Also new catalyst compositions are prepared by sulfiding nickel-containing compositions with carbonaceous sulfur containing compounds such as dialkylsulfoxides. Another embodiment of the invention is catalyst and dehydrogenation therewith, in which pores having radius of 50 to 200 Angstroms occupy pore volume from 0.30 to 1.50 ml per gram of the support, and pores having radius of 20 to 50 Angstroms occupy pore volume less than 0.1 ml per gram of the support. In another embodiment, alkanes are dehydrogenated using as catalyst a metal or metal compound having dehydrogenating activity supported on alkali-treated alumina.

30 Claims, 7 Drawing Sheets

PROCESS AND CATALYST FOR DEHYDROGENATION OF ORGANIC COMPOUNDS

BACKGROUND OF THE INVENTION

This invention relates to catalytic dehydrogenation of $C_3$ to $C_{10}$ alkanes, especially normal or isobutane or methylbutanes or other dehydrogenatable hydrocarbons, ethylbenzene for example.

Known processes for dehydrogenation of $C_3$–$C_{10}$ alkanes to monoolefins are capital intensive and demand high operating costs because of severe energy requirements. Many of the existing processes for dehydrogenation of alkane fractions, particularly $C_3$ to $C_5$ fractions, to monoalkenes use catalysts which rapidly deactivate and require frequent or continuous regeneration. This need often leads to additional process complexity or to large reactor volumes or low on-stream factors. The development of selective and economical processes to provide mono-alkenes from alkanes will facilitate the production of reformulated motor fuels, the utilization of low value high vapor pressure components in motor fuels, and the production of chemical products which are in high demand.

Conventional dehydrogenation processes have high operating and capital costs: The need for feed dilution and the unfavorable position of the equilibrium, resulting in relatively low conversion, necessitate large reactor vessels, which adds to capital costs. Furthermore, the requirement of frequent catalyst regeneration necessitates a further increase in reactor volume (numbers of vessels in parallel or a separate additional regenerator vessel) to enable concurrent or periodic regeneration of catalyst. Alternatively, as in the Oleflex or Snamprogetti-Yarsintez processes, a stream of catalyst can be circulated between the main reactor and a regeneration vessel continuously. This requires a complex physical arrangement and mechanical control system and suffers from the requirement of additional catalyst inventory. An expensive precious metal based catalyst may be used, and catalyst attrition during circulation may result in further catalyst expense or the need for equipment to prevent environmental contamination from catalyst fines. An additional disadvantage of typical dehydrogenation processes is the high temperature of operation which is required to maximize the product in these equilibrium limited systems. The high endothermicity of dehydrogenation requires a large heat input which in turn results in high capital costs for heaters, heat exchangers, reheaters etc, as well as in high operating costs for fuel. Oxidative dehydrogenation processes in which an oxygen source is a coreactant overcome the costs associated with low conversion and high heat input requirements, but known oxidative dehydrogenation processes are generally not sufficiently selective to monoalkenes, particularly when normal alkanes are used as a feedstock. The present invention overcomes many of the problems associated with the known art.

PRIOR ART

Processes in which catalytic dehydrogenation is followed by catalytic selective oxidation of hydrogen are disclosed in T. Imai et al, AICHE Nat. Mtg., New Orleans, March 1988, Preprint 64a, in T Imai et al U.S. Pat. No. 4,788,371 and R. A. Herber et al U.S. Pat. No. 4,806,624, Process in which hydrogen is cofed with alkane feedstock is disclosed in Miller U.S. Pat. No. 4,727,216 issued Feb. 23, 1988.

Processes in which alkanes are hydrogenolyzed using nickel and copper-containing catalysts are disclosed in Carter et al, U.S. Pat. No. 4,251,394, issued Feb. 17, 1981, J. H. Sinfelt et al, *J. Catal.* (1972), 24, 283, J. A. Dalmon et al, *J. Catal.* (1980), 66, 214, Z. Popova et al, *React. Kinet. Catal. Lett.* (1989), 39, 27 and D. Nazimek, *React. Kinet Catal. Letter* (1980), 13, 331. Other references disclosing using nickel/copper catalysts for other reactions are B. Coughlan et al, *J. Chem. Techm. Biotechnical* (1981), 31, 593 and S. D. Robertson et al, *J. Catal.* (1975), 37, 424.

Catalysts consisting of chromia supported on alumina are disclosed for use in dehydrogenation in U.S. Pat. No. 4,746,643 issued in 1988. Chromium treated silicas and silica-titanias are known as olefin polymerization catalysts, P. McDaniel et al, *J. Catal.* (1983), 82, 98; 110; 118. Additional prior art is described below.

EMBODIMENTS OF THE INVENTION

The invention provides ways of overcoming the disadvantages of the prior art dehydrogenation of alkanes and provides improvements in the results obtained in prior art processes. The invention has seven general embodiments, each of which is further divided into sub-embodiments.

In the first embodiment, the invention relates to a multi-step process flow scheme which conserves heat by alternating endothermic dehydrogenation zones and at least one exothermic zone in which hydrogen is selectively oxidized; in this scheme, any known dehydrogenation catalyst and any known catalyst for selective oxidation of hydrogen can be used.

In the second embodiment of the invention, particular dehydrogenation catalysts are used in dehydrogenation of dehydrogenatable compounds generally whether or not according to the process flow scheme according to the above embodiment of the invention. These catalysts are sulfided catalysts containing nickel and an optional modifier such as compounds or allotropes of tin, chromium, copper or others described infra on a support of little or no acidity, for example supports such as a sodium-exchanged or barium-exchanged zeolite, such as zeolite L or mordenite, or a cesium-treated alumina; sulfiding is particularly effective with preferred reagents described below in another embodiment of the invention; preferred catalysts also have particular pore structures, described infra and prepared according to yet another embodiment. An optional barrier layer, described below, may also be incorporated.

Nickel with optional addition of modifiers may also be supported on a support consisting of a metal oxide such as alumina of a particular pore size distribution which has been precoated with a carbonaceous layer containing little or no hydrogen. All of the nickel catalysts described above require activation prior to use, including a sulfiding step.

In a preferred mode of this embodiment, catalysts are activated by sulfidation in the presence of molecular hydrogen using particular reagents, consisting of compounds containing both carbon and sulfur atoms, preferably within certain ratios, and optionally containing oxygen atoms such as in dimethylsulfoxide. This treatment is followed by a coking procedure to provide an additional carbonaceous component to the catalyst, preferably within certain ranges of weight percent carbon. This overall procedure results in catalysts which exhibit outstanding selectivity and activity in the dehydrogenation processes summarized above; inferior performance is observed if hydrogen sulfide is used as a sulfiding agent exclusively.

The catalysts may be further improved by adjusting the acidity of a support. For example, the acidity of alumina may be reduced by treatment with alkali components and, optionally, calcination to suppress coking, hydrogenolysis, and isomerization when the resulting support is used in the preparation of a dehydrogenation catalyst which is used according to the invention.

An optional procedure may also be applied to provide for an intermediate barrier layer between the support oxide and the nickel component. This layer inhibits one type of deactivation by slowing the formation of inactive compounds between nickel and the bulk support oxide. For example, a refractory metal aluminate layer may be preformed on an alumina support by impregnating the support with a metal-containing material, an organometallic compound for example, and calcining the impregnated support at a temperature, 500° C. for example, at which a metal aluminate layer is formed on the support. Then the support containing the metal aluminate layer is impregnated with an active metal-containing material and calcined at a lower temperature, 200° C. for example. The preformed metal aluminate layer inhibits further reaction between alumina and nickel during catalytic processing steps using this catalyst.

In the third embodiment, useful catalysts are prepared by a combination of leaching of solid metal oxide supports with liquid solutions containing carboxylic acids, for example oxalic acid, and calcination. This process adjusts support pore structure distributions to preferred ranges which, among other benefits, increases the tolerance of the catalyst to coke deposition and enables relatively severe reaction conditions to be used without undue deactivation of the catalyst. The preferred pore size ranges are described infra.

A temporary pore blocking reagent can then be impregnated selectively into the remaining small pores to block access to small pores during impregnation with a liquid solution containing a nickel compound in a solvent which is immiscible or poorly miscible with the temporary pore filling reagent. This technique results in a skewed nickel deposition after drying and subsequent treatment such that a higher nickel concentration is deposited within larger pores than within pores of smaller radii. These supported nickel materials are then sulfided and further activated, as described in detail later, and become catalysts of long useful lives on-stream and of high selectivity as illustrated in examples. This pore blocking technique is applicable to porous supports generally, for temporary blocking of the smaller pores in the support.

In the fourth embodiment, an effective dehydrogenation catalyst consists of sulfided nickel supported on a carbon coated metal oxide support which also features a particular pore size distribution. Compositions of this type are superior to typical bulk carbon supported nickel catalyst which do not contain a pore modified metal oxide, in their effective useful on-stream lives when used in dehydrogenation processes according to this invention.

In the fifth embodiment, a Group IVB or VB metal phosphate such as tin phosphate is used to catalyze the selective oxidation of hydrogen in a mixture thereof with hydrocarbons and a source of oxygen. The Group IVB or VB metal phosphate catalyst can be incorporated on the surface of or within the pore structure of an otherwise inert porous monolithic ceramic body with efficient heat transfer properties. Other support structures such as the bonded porous metal bed described in European patent application EP416,710 and incorporated herein by reference, may also be used. Alternatively neat formed particles of the dried gelled catalysts may be used; preformed porous inert supports may be impregnated by the catalyst precursors, then calcined to form active catalysts.

In the sixth embodiment, the sulfided, non-acidic, nickel-containing dehydrogenation catalysts of this invention as described above and optionally prepared by the methods described above, are used in a particular multi-step process for dehydrogenation of dehydrogenable hydrocarbons, particularly $C_3$–$C_5$ alkanes, in which endothermic dehydration zones containing the nickel catalyst alternate between hydrogen combustion zones which contain hydrogen combustion catalyst and to which a source of oxygen is fed. Hydrogen may be cofed along with hydrocarbon feed, preferably within the range of 0.2 to 1.2 moles of hydrogen per mole of hydrocarbon feed, and most preferably within the range of 0.3 to 0.6 mole of hydrogen per mole of hydrocarbon.

In the seventh embodiment, the multi-step process described above in which dehydrogenation reactor zones alternate with hydrogen combustion zones is performed using particular dehydrogenation catalysts of this invention consisting of sulfided nickel on non-acidic supports and/or particular hydrogen combustion catalysts of this invention, supra. This embodiment, which requires the use of particular catalysts both for dehydrogenation and also for hydrogen combustion as well as a particular process flow scheme and reactor type, results in economic advantages when compared to other known dehydrogenation processes.

Each of the embodiments summarized above is described below in greater detail and with the help of examples.

DESCRIPTION OF THE DRAWINGS

The invention will be further described with reference to the attached drawings, in which.

MULTI-STEP PROCESS

Figure 1:
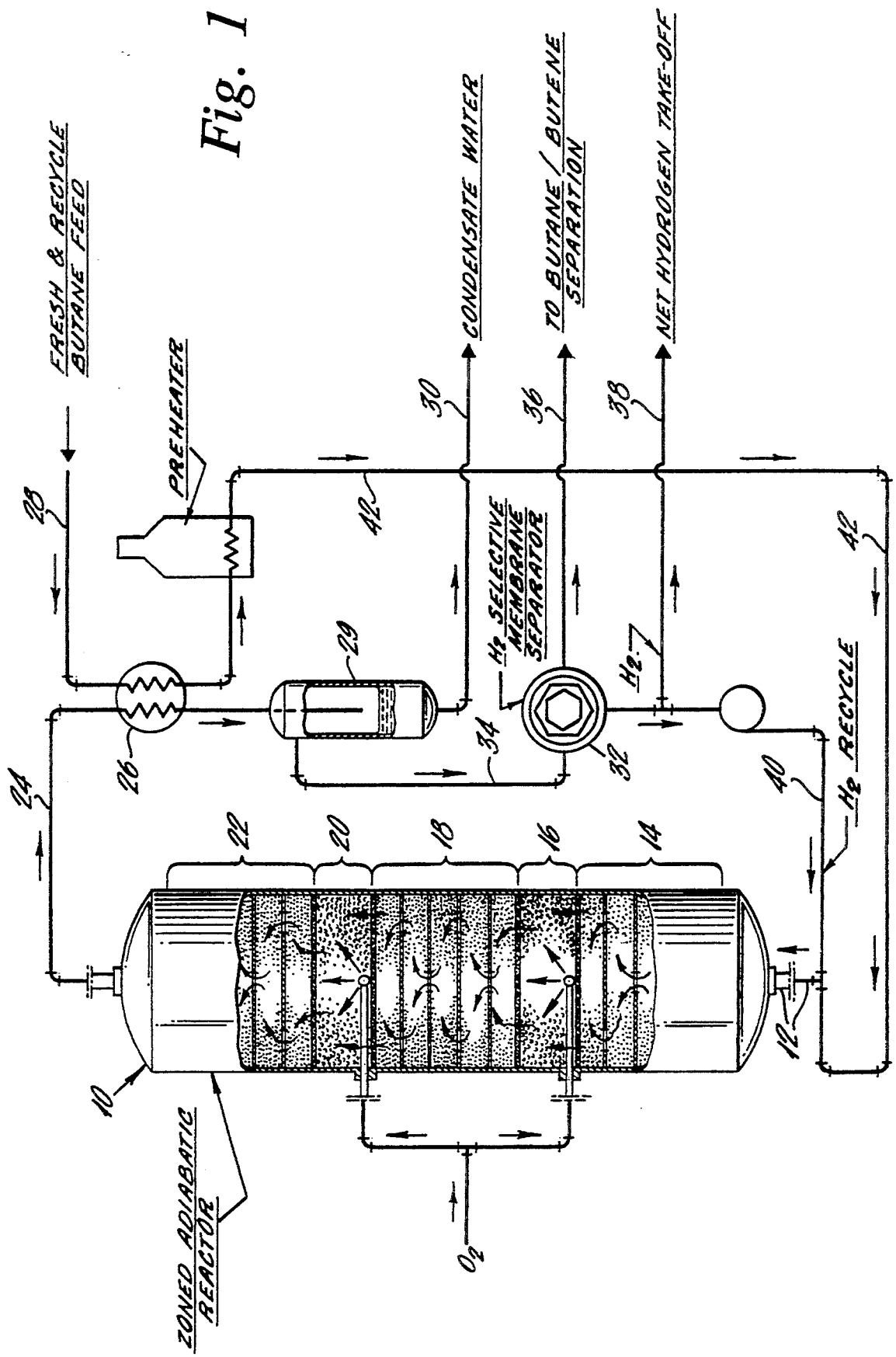
FIG. 1 illustrates a dehydrogenation process in which dehydrogenation zones alternate with zones in which hydrogen is selectively oxidized to generate heat for the next dehydrogenation zone.

The invention is, in the first embodiment as listed supra, a multi-step process for dehydrogenation of alkanes in which alkane plus hydrogen mixtures are passed through alternating endothermic catalytic dehydrogenation zones and at least one exothermic catalytic oxidation zone. These zones may be incorporated within a single reaction vessel so as to provide an adiabatic or near adiabatic reaction environment.

In the multi-step process embodiment of the invention, alkane-containing feed is contacted with dehydrogenation catalyst in each of a plurality of dehydrogenation zones to produce hydrogen and dehydrogenated hydrocarbon product. The hydrogen and dehydrogenated products produced are then contacted with oxidation catalyst and an oxygen-containing gas in each of said oxidation zones to selectively oxidize a portion of the stream and generate heat. The effluent from each oxidation zone along with heat produced are then routed through another dehydrogenation zone to produce additional hydrogen and dehydrogenated product. Hydrogen is separated from the reactor effluent in a separate process step using techniques known in the art, and a portion of the separated hydrogen is recycled with fresh feed and/or unreacted hydrocarbon feed to a dehydrogenation zone, preferably the first such zone in the adiabatic reactor train. Infrequent periodic regeneration of the dehydrogenation catalyst may be performed by passing an oxygen containing gas through the dehydrogenation catalyst zones as well as the oxidation catalyst zones for a time sufficient to remove excessive coke deposits, but not all coke deposits, followed by passing hydrogen and certain sulfur compounds through this zone to reactivate the catalyst.

In one embodiment of the multi-step process of the invention, there are two dehydrogenation zones and one catalytic oxidation zone. The products from the first dehydrogenation zone, which are reduced in temperature because of the endothermic nature of the dehydrogenation process, are contacted with oxidation catalyst in the oxidation zone to selectively oxidize a portion of the hydrogen in the product mixture, leaving hydrocarbons in the product mixture mainly unoxidized to oxygenated or combustion products. The selective oxidation generates heat which prepares the mixture for dehydrogenation of undehydrogenated alkanes remaining in the mixture, in the second dehydrogenation zone. Some heat may also be transferred to the preceding dehydrogenation zone; water and hydrogen are removed from the product mixture from the second dehydrogenation zone; and a portion of the removed hydrogen is recycled to the first dehydrogenation zone.

In other embodiments of the multi-step process of the invention, additional alternating dehydrogenation and oxidation zones are provided. For example, three dehydrogenation zones alternate with two oxidation zones. The products from the second dehydrogenation zone contain undehydrogenated alkanes, and the product mixture is reheated in the second oxidation zone by selective oxidation of hydrogen therein, and the reheated product is further contacted with dehydrogenation catalyst in the third dehydrogenation zone. Water and hydrogen are separated from the products from the third dehydrogenation zone, and a portion of the hydrogen is recycled to the first dehydrogenation zone. This is the operation shown in FIG. 1 described below. More than three dehydrogenation zones and more than two selective oxidation zones are within the scope of this embodiment of the invention, but are not preferred.

The catalyst employed in the dehydrogenation zones in the multi-step process according to this embodiment of the invention may be any known catalyst for dehydrogenation of alkanes, such as for example the catalysts disclosed in Miller U.S. Pat. No. 4,726,216 (Feb. 23, 1988). Alternatively, the catalyst may be one of the dehydrogenation catalysts described infra whose use in dehydrogenation processes generally is part of this invention. Alternatively, the catalyst may be one of the novel catalysts described infra.

In one embodiment, the catalyst employed in the oxidation zones of the multi-step process of this embodiment of the invention, for selective oxidation of the hydrogen component without burning much of the monoolefin or alkane in mixtures of hydrogen and hydrocarbons, may be any known catalyst for such selective oxidation, such as for example the catalysts disclosed as useful in the StyroPlus process as disclosed in T. Imai et al supra or in the Miller patent supra or the Pt/Sn/Cs/$Al_2O_3$ catalyst described in T. Imai et al U.S. Pat. No. 4,788,371 (Nov. 29, 1988).

In another embodiment, the catalyst employed in the oxidation zones for selective combustion of hydrogen can be the novel catalysts described infra whose use is part of this invention.

In one embodiment of the invention, a cofeed of hydrogen and optionally ppm levels of $H_2S$ are passed along with the alkane over the novel dehydrogenation catalyst of this invention; at particular hydrogen to alkane ratios, as subsequently disclosed, the ratio of initial dehydrogenation rate to average catalyst deactivation rate is maximized. Operations using preferred ratios of hydrogen to alkane, with the novel catalysts of this invention infra, result in optimal alkene yield over the on-stream life of the catalyst between regenerations, and obviate the need for frequent regeneration to remove coke on catalyst. Hydrogenolysis over the novel catalysts of this invention, infra, is suppressed by at least initial sulfiding with particular reagents and by appropriate catalyst design. A single initial sulfidation of the novel catalysts after each oxidation cycle in our process using preferred reagent is usually favored, but under some circumstances continuous sulfidation with sources of sulfur such as hydrogen sulfide or other sulfur-containing compounds is acceptable after initial sulfidation with a particular type of sulfur compound. Sulfur-containing impurities in the feedstock may serve the purpose of providing continuous sulfidation.

In the multi-step process according to one embodiment of the invention, reactants, product olefins, feed hydrogen, and additionally produced hydrogen leave the dehydrogenation zone of a compound adiabatic packed-bed reactor and pass into a zone in which a portion of the hydrogen is selectively burned. Internal heat is provided in the right amount to balance the heat requirement for dehydrogenation and make the process thermoneutral. Typically, the hydrogen oxidation is controlled by the air or oxygen inlet rate such that about half or less of the hydrogen produced by dehydrogenation is consumed, since the heat of exothermic hydrogen oxidation is about twice that of the endothermic dehydrogenation. The heat produced via the exoergic hydrogenolysis reaction to yield principally methane by-products satisfies a portion of the heat input required for dehydrogenation and serves to reduce the amount of hydrogen required to be combusted in the oxidation zone. Hence the process is a net producer of hydrogen. Successive stages of hydrogen oxidation followed by dehydrogenation are stacked within the reactor. The hydrogen combustion zones should be sufficiently large to enable complete consumption of oxygen since breakthrough of oxygen into the dehydrogenation zone is detrimental. Porous ceramic hydrogen combustion zones may be used. The hydrogen combustion catalyst is contained within the pore structure of the catalyst support or on the surface of a ceramic monolith or is used neat. Oxygen may be fed orthogonally through the ceramic structural pores so that bulk mixing of either product or feed hydrocarbons or of hydrogen does not occur with oxygen prior to contact with active catalyst surface. Using the novel catalysts of this invention, the volume ratio of the combustion zone catalyst to dehydrogenation zone catalyst will preferably be 0.1 to 0.25 if packed beds of similar packed bed density are utilized in both zones.

According to the multi-step embodiment of the invention, at least two dehydrogenation zones and at least one selective oxidation zone may be employed in alternating fashion; larger numbers of such zones may also be used. A number of zones of unequal size may be interspersed in the reactor to maintain even heat distribution despite diminished heat absorption with each successive dehydrogenation stage as dehydrogenation equilibrium is approached. The worsened position of equilibrium due to mass action toward the reactants caused by hydrogen addition may be compensated for in part by the shifted position of equilibrium toward the product olefins as hydrogen is burned.

Control of the temperature in the dehydrogenation zones may be accomplished by adjustment of the feed rate and/or the oxygen concentration of the oxygen-containing gas to the hydrogen combustion zones. A diluent gas, for example, steam, may be fed along within the oxygen-containing gas into the combustion zones. Preferred temperature of operating the dehydrogenation zones varies depending on the feedstock, but is typically between 500° C. and 630° C.

Any means of separation of hydrogen from hydrocarbons and water can be used in the process such as the hydrogen recycle loop shown in FIG. 1. For example, membrane separation, pressure swing absorption techniques, or turboexpander techniques can be used. Capital cost requirements dictate the method of choice. Other aspects of the process hardware of the invention such as pumps, compressors, heaters, etc. are those generally useful and suitable.

Other processes are known which pass oxygen into a dehydrogenation reactor to selectively burn hydrogen. These include the "StyroPlus" process for ethylbenzene dehydrogenation (see Imai et al AIChE Nat. Mtg., New Orleans, 3/88 Preprint 64a 20p supra; *Process Engineering* (London),(1988), 69, 17), and the process disclosed in R. A. Herber et al, U.S. Pat. No. 4,806,624 (Feb. 21, 1989). The present process differs in one embodiment from these known processes by virtue of circulating additional hydrogen beyond that which is produced by catalytic dehydrogenation and of not requiring substantial quantities of additional steam cofeed along with hydrocarbon feed. Steam generation is expensive and forces the use of larger reactor vessels due to the high steam to hydrocarbon ratios required in the Herber et al patent. The additional hydrogen and the particular hydrogen to hydrocarbon ratio of our preferred embodiments result in greater time on stream between regenerations, enabling economical operation, a factor not recognized in the Herber et al patent.

Dehydrogenation in the presence of hydrogen cofeed is disclosed in the Miller patent supra. The disclosed procedure of this patent does not however require nor recognize the advantage of selective hydrogen combustion. Another distinguishing feature of one embodiment of this invention is the use of catalysts as subsequently described, for optimum performance. The subsequently described catalysts may be more selective and have greater onstream life than the catalyst of the Miller patent when dehydrogenating in the presence of hydrogen cofeed, particularly at the preferred hydrogen to alkane feed ratios of the invention. Also, the catalysts of the invention, using nickel plus other lesser quantity of modifier, rather than platinum as in the Miller patent are expected to have lower material costs. The process of the invention uses a sulfided catalyst, but as disclosed below, uses in one embodiment a sulfiding agent not suggested in the Miller patent supra, thereby obtaining longer onstream life and shorter induction periods during which the catalyst is activated.

Imai et al U.S. Pat. No. 4,788,371 supra discloses alternating dehydrogenating and hydrogen oxidation zones (column 10, lines 22–28) but uses the same catalyst in all zones, whereas applicants' process advantageously uses different catalysts in the dehydrogenation and hydrogen oxidation zones. Imai's dehydrogenation process is typically conducted in the presence of a large amount of steam, the ratio of steam to hydrocarbon being 2.07 moles of steam to 0.7 mole of hydrocarbon in Table 1 for example; whereas, applicants' process preferably uses no added steam, or no more than 0.5 mole of steam per mole of hydrocarbon. Added steam, if used in applicant's process is a minor amount of the reaction mixture. Use of hydrogen as in applicants' process is more effective against coking of the catalyst than the use of steam.

The Herber et al patent supra discloses catalytic dehydrogenation of hydrocarbons, followed by catalytic selective oxidation of hydrogen in the dehydrogenation product and indirectly heat exchanging the oxidation product with fresh feed to the dehydrogenation to preheat the latter; the oxidation zone effluent stream is not contacted with dehydrogenation catalyst. In applicant's process, the oxidation product is passed into a second dehydrogenation zone to dehydrogenate feed hydrocarbon which was not dehydrogenated in the first dehydrogenation zone. In one embodiment of applicant's invention, for better control of the overall reaction, the temperature differential in each of the dehydrogenation zones is less than 25° C. between the inlet and outlet of the zone, and a sufficient number of dehydrogenation zones is used to obtain the desired overall conversion.

Imai et al, The Principle of Styro Plus, AIChE Nat. Mtg. New Orleans, 3/88, Reprint 64a, supra, discloses alternating steam dehydrogenation and hydrogen oxidation zones (page 6). The dehydrogenation catalyst is apparently a potassium promoted iron catalyst (page 5). The selective oxidation catalyst is a proprietary catalyst, apparently different from the dehydrogenation catalyst. The feed to the first dehydrogenation zone apparently consists of steam and hydrocarbon. The hydrogen produced in a dehydrogenation stage is more than enough to provide, by selective oxidation thereof, the heat needed for the next dehydrogenation stage. Apparently, no additional hydrogen is supplied to the process. Applicants' process uses only minor amounts of steam at most, and supplies additional hydrogen to the dehydrogenation process.

CATALYTIC DEHYDROGENATION WITH PARTICULAR CATALYSTS

In this embodiment, the second as listed above, the invention relates to catalytic dehydrogenation of dehydrogenatable hydrocarbons, particularly $C_3$–$C_{10}$ alkanes, with particular catalysts which can be used in the novel process of this invention supra, or in any dehydrogenation process which is conducted in the presence of added hydrogen such as the Oleflex dehydrogenation process or catalytic reforming for example. When the catalysts of this invention are sulfided, infra, it is convenient to replace with the catalysts of this embodiment only the last section of catalyst in a motor fuel reforming operation so that spilled over sulfur does not contaminate other sulfur sensitive catalysts such as platinum or platinum-rhenium formulations normally required for aromatization.

The dehydrogenation catalysts of this embodiment comprise combinations of a nickel component and one or more optional modifiers as described below, supported on non-acidic supports of a type which preferably exhibit a prescribed pore structure, and activated by reduction, sulfiding with particular type of reagent, and optionally precoking. For optimal catalyst performance, preferred combinations and ranges of the non-nickel (modifier) component, the pore structure of the support, the pretreatment of the support, and the method and reagents for activation of the catalysts are used, as subsequently disclosed.

The loading ranges for the nickel component can be 0.5 to 25 weight percent nickel, preferably 2 to 12 weight % Ni, and most preferably 4 to 9 weight % Ni.

In addition to a nickel component, modifier components may be added to the catalyst. The modifier component(s) may serve the purpose of maintaining the dispersion of the nickel component during use, of altering catalyst activity or selectivity by alloying with or otherwise directly interacting with the supported nickel component, of adjusting the surface acidity of an underlying metal oxide support, of gasifying coke which has formed as a side product during use of the catalyst for dehydrogenation, of providing an activating support layer between the nickel and bulk oxide support, or by acting as a refractory intermediate layer which slows further reaction between the nickel and bulk oxide support to catalytically inactive compounds. The particular class of modifier which serves as an intermediate layer which hinders reaction of supported nickel with the underlying bulk oxide support particularly during use of the catalyst in a regeneration cycle in which coke is burned off, is referred to as a barrier layer, described below.

Useful modifiers are compounds or allotropes of lithium, sodium, potassium, rubidium, cesium, beryllium, magnesium, calcium, strontium, barium, chromium, molybdenum, tungsten, copper, silver, gold, palladium, rhenium, iridium, tantalum, vanadium, iron, indium, tin, antimony, lead, bismuth, arsenic, titanium, zirconium, cerium, lanthanum, or phosphorus. Modifiers may be incorporated within the support.

The range of copper, tin or lead modifier to nickel atomic ratios used in this embodiment of the invention is typically 1 to 80 atomic percent modifier. The preferred range is 6 to 75 atomic % modifier; the most preferred range is 55 to 65 atomic % when the modifiers are Cu or Sn or Sb or Bi or Pb. The limits of the ranges may vary when the modifiers are Ba, Sr, Ca, Mg, Be, Li, Na, K, Rb, Cs, P or other modifiers; suitable ranges may be determined by a person skilled in the art in the light of this specification.

Supports generally useful for this embodiment of the invention are any non-acidic support or supports treated to reduce acidity either before, during, or after incorporation of nickel. Useful supports include leached aluminas of reduced acidity, silicas, zirconia, titania, magnesia, chromium treated silicas or silica-titania, tantalum doped zirconia as described in copending Durante et al application Ser. No. 07/743,658 filed Aug. 12, 1991 now U.S. Pat. No. 5,221,464, the disclosure of which is hereby incorporated by reference, non-acidic forms of zeolites, such as base treated mordenite or barium exchanged zeolite, microporous aluminum phosphates, nonacidic forms of SAPO's (silicoaluminum phosphates), silicoferrates, silicoborates, silicotitanates, other non-acidic molecular sieves, basic clays, magnesium-aluminate spinel, zinc aluminate, carbon coated supports, ceramics, and other supports known in the art. The choice of a support is affected in the case of our preferred compositions by a performance range in a particular acidity test, by a favorable pore size distribution as specified below, and by stability to process conditions.

Physical properties such as density are also considered depending on the nature of the process reactor application. Acidity reduced, pore-modified aluminas are preferred over the molecular sieve supports for process conditions resulting in high coke levels between catalyst regneration cycles. In cases of low temperature operation, molecular sieve or siliceous supports may be favored.

The support optionally may be pretreated not only to reduce acidity, but also to effect a particular nickel distribution, to adjust the pore structure, as described in another embodiment infra, or to provide for a surface barrier layer which hinders reaction of the active portion of the nickel component with the bulk support phase during cyclic oxidation-reduction treatment or during oxidative regeneration of the catalyst. Any suitable physical form of the support for the process in question may be used such as microspheres prepared by spray drying, extrudates, monoliths, beads, rings, etc.

LOW ACIDITY DEHYDROGENATION CATALYST

A required feature of the catalyst of this embodiment is low acidity. Typical transition phase alumina-based supports are too acidic for direct use in these preparations. When aluminas are used as supports, significant reduction in acidity can be achieved by treatment of the alumina with alkali components. Reduction in surface acidity promotes low coking rates, low hydrogenolysis rates, and, particularly low isomerization rates.

The alkali components may be selected from the group of compounds or allotropes of cesium, rubidium, potassium, sodium, lithium, or francium, or mixtures thereof. Potassium, rubidium or cesium, or mixtures thereof are preferred alkali components. Preferably, the alkali component is well dispersed throughout the catalyst. The addition of alkali components may be accomplished by impregnation prior to or after the incorporation of nickel or in a coimpregnation step. They may also be incorporated by a coprecipitation method which often results in a mixed alumina-alkali structure after calcination in the case of aluminiceous supports. Other methods of incorporating the alkali that may be used are cogelation and ion exchange.

We prefer to add the alkali component separately from nickel in order to non-homogeneously distribute nickel with regard to pore structure (vide infra) yet uniformly deposit the alkali on the support surface.

The preferred alkali loading depends on the method of incorporation and the surface area of the support, for example alumina. When using cesium as the alkali, typically useful ranges are 1 to 8 weight percent cesium loading. Preferred cesium loading range for a 90 m$^2$/g precalcined and preleached alumina (vide infra) to contain 6–8% nickel loading, is 5 to 7% by weight.

In preparing zeolite supports, ion exchange or impregnation methods to remove protonic acidity are effective. Base treated mordenite or barium ion exchanged zeolite L are useful supports, for example. In the case of barium ion exchanged L zeolite, for example, repetitive ion exchange-calcination steps are required to reduce acidity substantially, as illustrated in Example 13 infra. After incorporation of nickel, modifier, sulfidation, and activation, sufficiently basic supports result in virtually no isomerization and little hydrogenolysis of isobutane under laboratory test reaction conditions in which 2 moles of hydrogen are cofed per mole of isobutane at 600° C. over a 10 ml bed of catalyst held isothermally. Further description of this aspect of the invention is illustrated in the examples below.

The non-acidic supports employed for the catalysts of this embodiment distinguish the same from the "bifunctional" catalysts typically used in naphtha reforming. The combination of preferred pore structures and preferred activation methods, along with low acidity, distinguish these catalysts from other supported nickel catalysts known in the art for hydrocarbon conversion processes.

J. H. Sinfelt, J. Carter and D. J. C. Yates, *J. Catal.* (1972), 24, 283, supra, disclose the hydrogenolysis of ethane to methane and the aromatization of cyclohexane to benzene over copper-nickel alloys.

J. A. Dalmon and G. A. Martin, *J. Catal.* (1980), 66, 214, supra disclose hydrogenolysis of ethane, propane and n-butane over silica-supported nickel-copper alloy catalysts.

Z. Popova et al, *React. Kinet. Catal. Lett.* (1989), 39, 27, supra, disclose hydrogenolysis using nickel- and copper-containing catalysts.

D. Nazimek, *React. Kinet. Catal. Lett.* (1980), 13, 331, supra, disclose copper admixture to the Ni/Al$_2$O$_3$ system and the use of the resulting catalyst in the hydrogenolysis of n-butane in the temperature range of 723–573K.

B. Coughlan et al, *J. Chem. Tech. Biotechnol.* (1981), 31, 593 disclose alkylation of toluene with methanol using bimetallic nickel/copper zeolite catalysts prepared from NaY and NH$_4$Y as starting materials. The catalysts are disclosed to be ineffective for the hydrogenation of benzene.

S. D. Robertson et al, *J. Catal.* (1975), 37, 424 disclose as prior work the oxidation of ethylene to ethylene oxide and of cumene to cumene hydroperoxide using a Ag/Au alloy catalyst, and hydrogenation of ethylene, benzene and butadiene using a Ni/Cu alloy, and as new work a study of the reduction characteristics of copper-, nickel- and copper-nickel-on-silica catalysts.

Although the invention in the use of a sulfided nickel catalyst supported on a non-acidic support containing optional modifiers is not to be limited by any theory of its mechanism of operation, we believe that the unwanted reaction of hydrogenolysis requires rather large ensembles of nickel to be rapid. Alloying of nickel with certain modifiers such as copper or tin reduces the incidence of large ensembles of nickel on the surface and acts to dilute the surface. Also hydrogen chemisorption on the surface is probably diminished relative to the unalloyed cases thereby reducing the effective hydrogen concentration and, consequently, the rate of hydrogenolysis on the surface. Sulfidation probably further reduces the size of available nickel ensembles. The lack of acidity ensures that only metallic or metal carbide activity, as opposed to acid-catalyzed activity is observed. The combination of these effects results in an increase in the rate of dehydrogenation relative to the rate of hydrogenolysis, hence in a selectivity improvement compared to a non-alloyed non-sulfided pure nickel catalyst.

In the case of the use of Ta—ZrO$_2$ supports, it is believed that there may be an electronic metal-support interaction which acts to suppress further the hydrogen chemisorption and the rate of processes such as hydrogenolysis which depend on the surface activity of hydrogen. Tantalum compounds may also assist in the gasification of coke formed as a side reaction of dehydrogenation processes.

DEHYDROGENATION CATALYST WITH SURFACE BARRIER LAYER

In addition to support acidity reduction, catalyst modifiers or, in some cases, excess nickel may be added in a separate preparation step followed by calcination so as to provide for an intermediate refractory layer between the portion of nickel component which is substantially active and the bulk support, termed a barrier layer. The barrier layer serves to lessen deactivation of the finished catalyst during use or to mitigate inactivation as a result of calcination during preparative steps by lessening bulk reaction between nickel compounds and the bulk support oxide. The barrier layer may also serve to maintain dispersion of nickel. Preferred catalyst formulations especially on non-molecular sieve supports contain a barrier layer. Barrier layers are especially preferred on aluminiceous supports on which nickel aluminate may otherwise form during calcination in air.

The formation of a barrier layer may be accomplished by treatment of the support prior to nickel loading with organozirconate or organotitanate reagents, preferably CAVCO MOD coupling agents sold by Cavedon Chemical Co. or alkoxytitanates such as TYZOR reagents sold by E. I. DuPont de Nemours Co., or other brand zirconium organofunctional compounds, tantalum compounds, or magnesium compounds, followed by drying and calcination in air at conditions sufficient to convert the barrier reagents to oxides or hydroxides. This treatment can be accomplished by methods known in the art and described in vendor literature.

Particularly with aluminiceous supports, other barrier layers may be produced by preformation of non-nickel aluminates such as copper aluminate, on a thin layer of the support surface prior to application of nickel. This technique is described by Kulkarni et al. in *J. Catal.* 131,491 (1991); the disclosure of which is incorporated herein by reference.

When a separate barrier layer is not applied to an aluminiceous support, deliberate preformation of a nickel aluminate layer may be desirable. This can be produced by repeated impregnation with nickel compounds—calcination steps such that the first calcination is above 500° C. in oxygen or air, followed by one or more subsequent impregnation-low temperature calcination steps, followed by optional heat treatment in reducing or inert atmospheres. Example 25 further describes this process.

On siliceous supports such as silica, silica gels, zeolites, and the like, a preferred barrier layer is provided by incorporation of surface-anchored chromyl species. We believe that the surface-anchored chromyl species provide a support environment for sulfided nickel which results in enhanced and longer lasting activity for alkane dehydrogenation, especially in the presence of hydrogen, than supports without the surface-anchored chromyl species. Without limitation to any theory, the activity maintenance of these catalysts may be related to the maintenance of nickel dispersion especially well in these Ni/Cr compositions with increasing time on-stream. The preparation of chromyl barrier layers is readily accomplished by pretreatment of siliceous supports with chromium compounds followed by calcination.

Chromium treated silicas and silica-titanias are known and are used commercially as olefin polymerization catalysts as described in M. P. McDaniel & M. B. Welsh, *J. Catal.* (1983) 82, 98; 110/118. Catalysts consisting of chromia supported on aluminas without nickel are also known for dehydrogenation. For example, such a catalyst is described in U.S. Pat. No. 4,746,643 (1988). Known methods of preparing surface chromyl barrier layers according to the above articles and patents are incorporated herein by reference. Examples 7, 8, 10 and 15 through 18 describe the preparation and testing of catalysts incorporating chromyl barrier layers.

CATALYST ACTIVATION

Another feature of the catalysts of this invention is their activation prior to use. The catalysts are preferably in a fully or partially reduced state, sulfided, and contain some amount of carbonaceous material. A preferred method of activation involves the use of carbon-sulfur compounds such as, for example, dimethylsulfoxide, in the presence of free hydrogen to provide the sulfur and carbon deposition required for activation.

Additional carbonization (coking) of the catalyst may also be conducted as part of the activation process as described infra.

These catalysts, once activated, have superior selectivity. They accelerate the dehydrogenation reaction while minimizing hydrogenolysis (hydrocracking), with resulting lower loss of feedstock to unwanted reactions and in greater product hydrogen purity, and reduced unwanted production of methane and the like. The catalysts are reasonably sulfur tolerant and can be used on untreated refinery feeds.

Prior art disclosures of sulfided Ni catalysts for dehydrogenation are: H. E. Swift, et al., *I&EC, Prod. R&D* (1976). 15, 133; of Ni—Sn catalysts, V. D. Stysenko, et al., *Kin. & Catal.* (translation) Russian original: (1987), 28, #4, Part 2, page 802, and M. Agnelli, et al. *Catalysis Today* (1989), g, 63; of Pt—Sn:Pt—In catalysts, Lyu Kam Lok, et al., *Kinetikai Kataliz.*, (1988), 29, #5, 1146, and S. D. Gardner, et al. *J. Catalysis*, (1989), 115, 132; and of Pt-L zeolite, J. R. Bernard, *Proceedings of the 5th International Conf. on Zeolites* (Naples), (1980), p. 686.

CATALYSTS FOR SEVERELY DEACTIVATING CONDITIONS

In further embodiments of the invention, improvements to supported nickel catalysts render the catalysts more useful in dehydrogenation processes. In addition to the previously disclosed general advantages of sulfided nickel catalysts over other known dehydrogenation catalysts, the preparations of these embodiments demonstrate additional improvements in performance which enable their use under what would ordinarily be severely deactivating conditions.

Severely deactivating conditions comprise operation at temperatures of greater than about 530° C., at hydrogen-to-alkane feed ratios of 2 or less, and/or a requirement for more than about 90 hours on stream between regenerations. Despite the increased rate of catalyst deactivation, operation in the severely deactivating mode is desired because it results in reduced capital costs and reduced operating expenses in some dehydrogenation processes such as the dehydrogenation process previously disclosed herein, particularly as a result of the reduced volume of hydrogen which is required to be cofed. This results in diminished compressor load, smaller reactor volumes and easier downstream separations.

The use of these improved catalysts in other dehydrogenation processes at operating conditions normally used for such processes results in extended catalyst life over what is typical for known catalyts.

Certain combinations of catalyst compositions and features are better suited than others when the catalysts are to be used under severely deactivating conditions. Preferred formulations of catalysts result in greater activity retention per given time-on-stream and easier regenerations, once the catalysts have been deactivated, to recover activity and selectivity. The preferred catalysts for use under severely deactivating conditions may also be used at milder operating conditions such as at higher hydrogen-to-alkane molar feed ratios than 2.

The catalysts of this embodiment which are preferred for use under severely deactivating conditions have one or more of the following characteristics:

1) a pore size distribution of the support such that there exists a greater pore volume than a specified minimum pore volume between certain (larger) pore radius boundaries and a lesser pore volume than a specified maximum limit between other (smaller) pore radius boundaries. This desirable overall pore structure may be achieved by a process of leaching and calcining the support phase when the support is alumina as described in a separate embodiment of the invention, infra.

2) reduced acidity achieved by doping the support with specific agents as described above.

3) optionally, a nickel distribution on the support favoring deposition in the larger pore radius region achieved by impregnating the support with a temporary pore filling agent.

4) optionally, a barrier treatment which hinders additional reaction between nickel and bulk support during the catalyst regeneration process such as to form nickel aluminate and hence stabilizes the catalyst against deactivation by reaction of the nickel with the support.

5) activation of the catalyst achieved by hydrogen reduction, sulfiding with a reagent containing both sulfur and carbon species, and precoking of the catalyst by forming a carbonaceous layer prior to running under steady state conditions.

6) activation of the catalyst by depositing coke or other organic compounds on a pore-modified support prior to addition of nickel and prior to hydrogen reduction, as described later in a separate embodiment of the invention.

The advantages of the novel preparations of these embodiments include:

1) greater activity retention per given time on-stream at low hydrogen to isobutane feed ratios (0.1–2 mol/mol) over catalysts previous disclosed 2) less susceptibility to pore plugging by coking than catalysts previously disclosed 3) lowered tendency towards feed isomerization, hence improved selectivity 4) ease of regeneration, once the catalysts are deactivated, to recover activity, selectivity and useful pore structure.

The inventions of these embodiments are the methods of making the catalysts, the process for use of these catalysts for dehydrogenation or oxidative dehydrogenation of alkanes, and in the case of precoked supports as subsequently disclosed, the composition of matter of the catalyst.

To realize optimal benefit from the catalysts of these embodiments of the invention, the temperature is preferably between 550° and 630° C. but other temperatures are also operative. Although a wide range of feed compositions can be used to advantage, a particular range of $H_2$/isobutane molar feed ratio, 0.3–0.5, may unobviously result in the largest ratio of initial dehydrogenation rate to average deactivation rate when isobutane is the feed hydrocarbon.

Various support compositions can be used as previously described herein, as well as formed clays and clay derivatives, mixed metal oxides, sintered ceramics, zeolites, etc., but a preferred support because of its ability to be modified, its stability in use, and ready availability and minimal cost is alumina in one of several phases. Our pore modification procedure described below is specific for alumina, but other supports can be modified utilizing the same principles but under somewhat modified leaching and calcination conditions within the skill of the art in the light of the disclosure herein. Furthermore, various macroscopic forms can be utilized such as spray-dried microspheres, extruded cylinders, spherical particles formed by the oil drop method, etc., depending upon the application.

PORE SIZE DISTRIBUTION OF CATALYST SUPPORT

Of importance in preparing catalysts with long lives under severely deactivating conditions (T>550° C.; $H_2$/hydrocarbon<2), is the distribution of pores in the support in the range 10 to 600 angstroms equivalent pore radii as measured by dynamic nitrogen desorption porosimetry and calculated assuming cylindrical pores. Since coke preferentially deposits in the region 20 to 40 angstrom pore radii, this embodiment of the invention minimizes the concentration of sulfided nickel component in pores in this size range. On the other hand, this embodiment increases porosity in the radius range of 50 to 200 angstroms, since this region still contributes significantly to surface area, yet is not as susceptible to pore blockage by coke. Porosity in pore radii greater than about 200 angstroms does not significantly enhance performance and may lead to a physical weakening of the structural integrity of the formed particles. Preferable porosities are:

| Radius Range (Angstroms) | Pore Volume, (ml/g) |
| --- | --- |
| 20 to 50 | less than about 0.1 |
| 50 to 200 | 0.30 to 1.50 |

Most preferable porosity ranges are:

| Radius Range (Angstroms) | Pore Volume (ml/g) |
| --- | --- |
| 20 to 50 | less than 0.05 |
| 50 to 200 | 0.40 to 0.80 |

Catalysts previously described based on zeolite supports, such as sulfided Ni/Cr/Ba-L zeolite, have non-optimal pore structures in the above ranges and are inferior to the pore-modified catalysts under severely deactivating conditions with regard to their useful on-stream lives.

Figure 2:
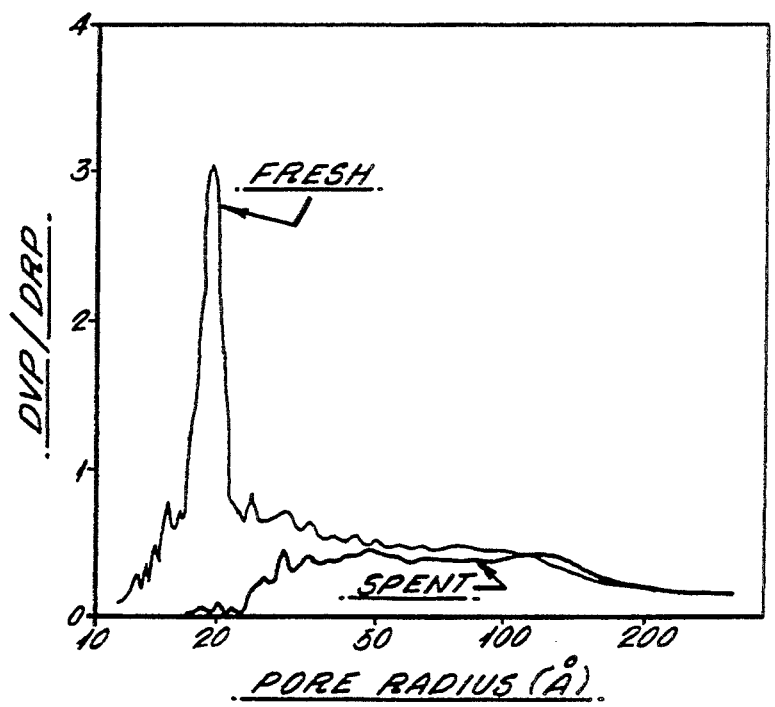
FIG. 2 shows the differential ratio of pore volume to pore radii, DVP/DRP, for fresh and for spent Ni—Cu/Ba L zeolite catalyst as a function of pore radius.
Figure 3:
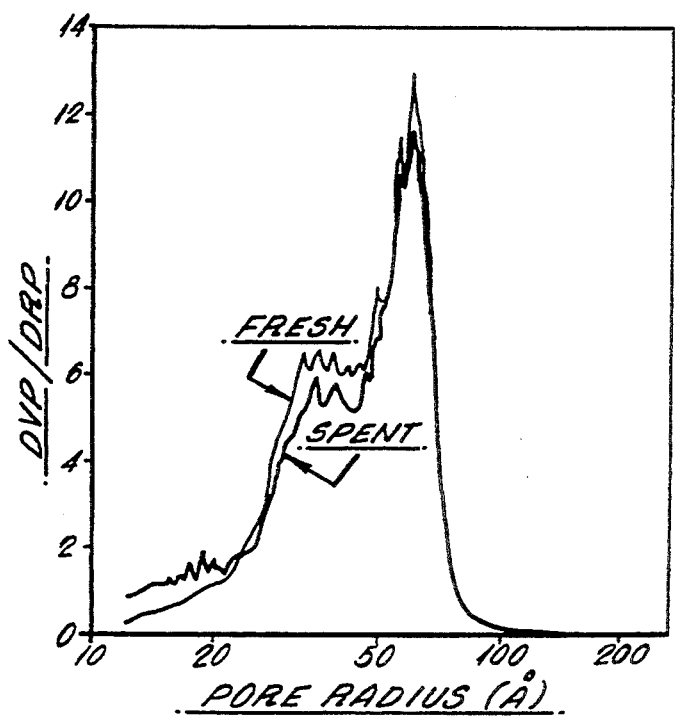
FIG. 3 is a similar chart for Ni—Cs/alumina catalyst having the pore radius distribution according to one embodiment of the invention.

FIGS. 2 and 3 of the drawings illustrate the different behavior of the two catalyst series. The pore volume diminution due to comparable amounts of coke deposition (about 1% by weight) is much more pronounced for the Ni—Cr/Ba L zeolite catalysts of FIG. 2 than for the preferred catalyst series with preferred pore structure of FIG. 3.

Figure 4:
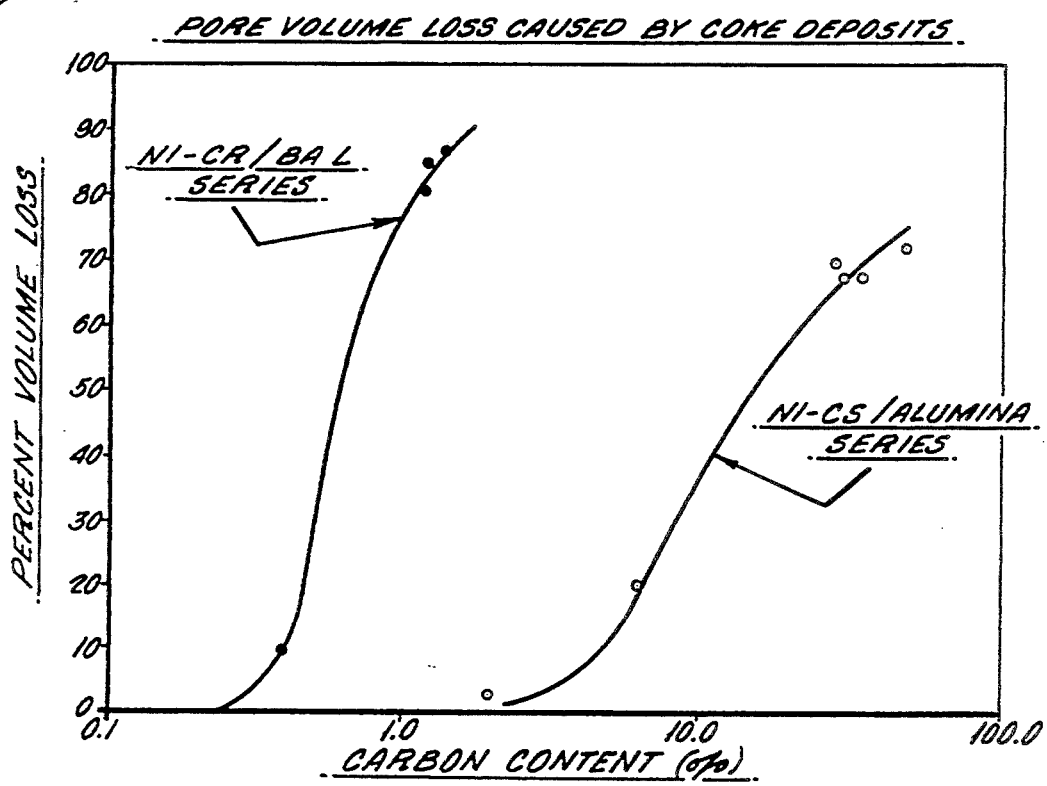
FIG. 4 shows percent pore volume loss caused by coke deposits as a function of carbon content for Ni—Cr/L zeolite catalyst and for Ni—Cs/alumina catalyst having the pore radius distribution according to one embodiment of the invention.

The improved tolerance to coke deposition of the new catalyst series as compared to the Ni/Cr/Ba-L catalyst series is illustrated in FIG. 4. The zeolite supported catalysts lose pore volume by the deposition of relatively small amounts of coke, while the new modified alumina supported catalysts tolerate much higher amounts of coke.

Figure 5:
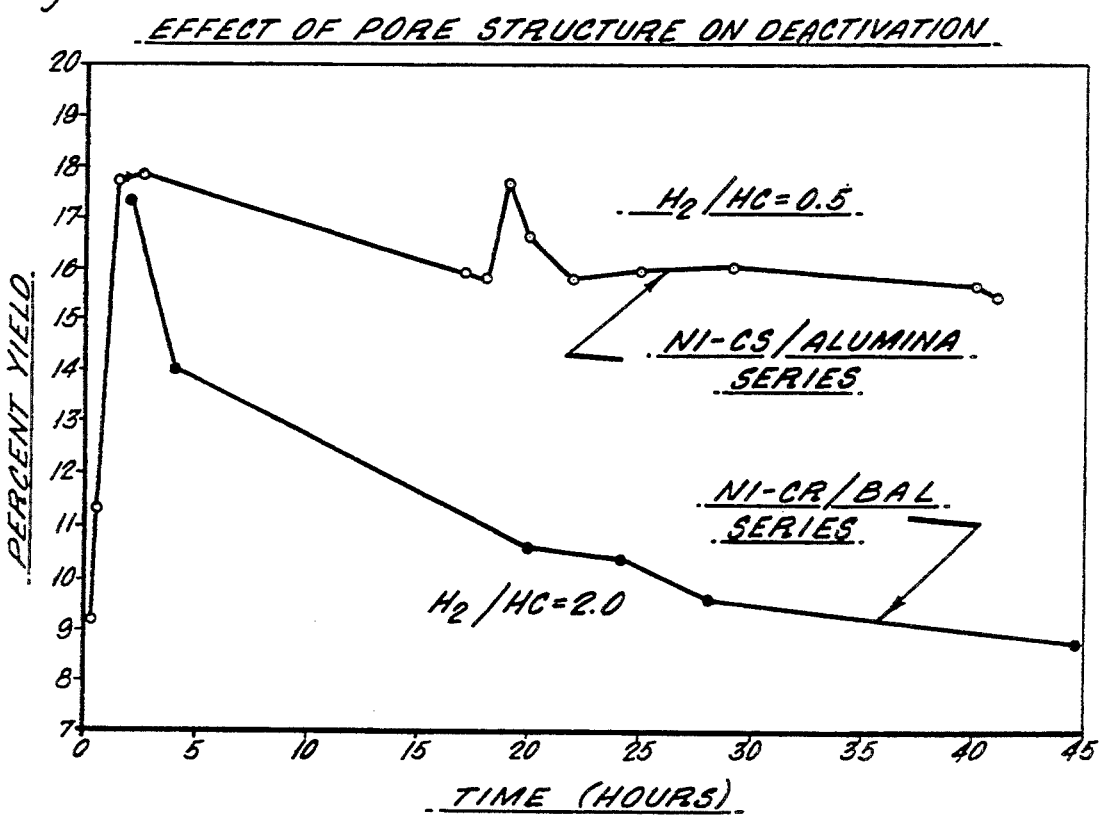
FIG. 5 shows the yield of dehydrogenated product as a function of reaction time for Ni—Cr/L zeolite at hydrogen to hydrocarbon mole ratio of 2.0 in a particular reactor system, and for Ni—Cs/alumina catalyst having pore radius distribution according to one embodiment of the invention, at hydrogen to hydrocarbon ratio of 0.5.

FIG. 5 is a comparison of relative activity loss in a dehydrogenation test reactor resulting from pore volume loss due to coking for a Ni—Cr/Ba-L non-pore size adjusted catalyst compared to a Ni—Cs modified alumina catalyst. The superior tolerance to coke of the latter catalyst is evident.

These figures indicate that certain pore size distributions affect the ability of supported nickel dehydrogenation catalysts to resist pore plugging and corresponding deactivation.

To further maintain activity, under severely deactivating conditions, catalysts having preferred pore structures may be loaded with nickel, or nickel plus modifier, such that there is a preferential deposition in the larger pore size regions. This is accomplished by temporarily filling the smaller pores with an organic liquid which is immiscible with or only slightly soluble in the impregnating solvent containing the nickel compound to be deposited. This is followed by impregnation with a nickel solution, drying and calcination steps. This preparation method and a resulting catalyst are further described in example 24 infra.

PRECOKING OF CATALYST

Following addition of the nickel component and modifier, the preferred catalysts of this embodiment of the invention are activated. We have previously described methods and reagents for reduction and presulfiding of the nickel which are effective to achieve suitable activities and selectivities. These steps are often accomplished in-situ once the catalyst has been installed in the reactor for the first time or after a regeneration cycle. In an improvement to this procedure, although coke formation leads ultimately to catalyst deactivation, a small amount of coke deposited onto the catalyst increases the activity of the catalyst. Hence, a precoking step activates the catalyst.

Figure 10:
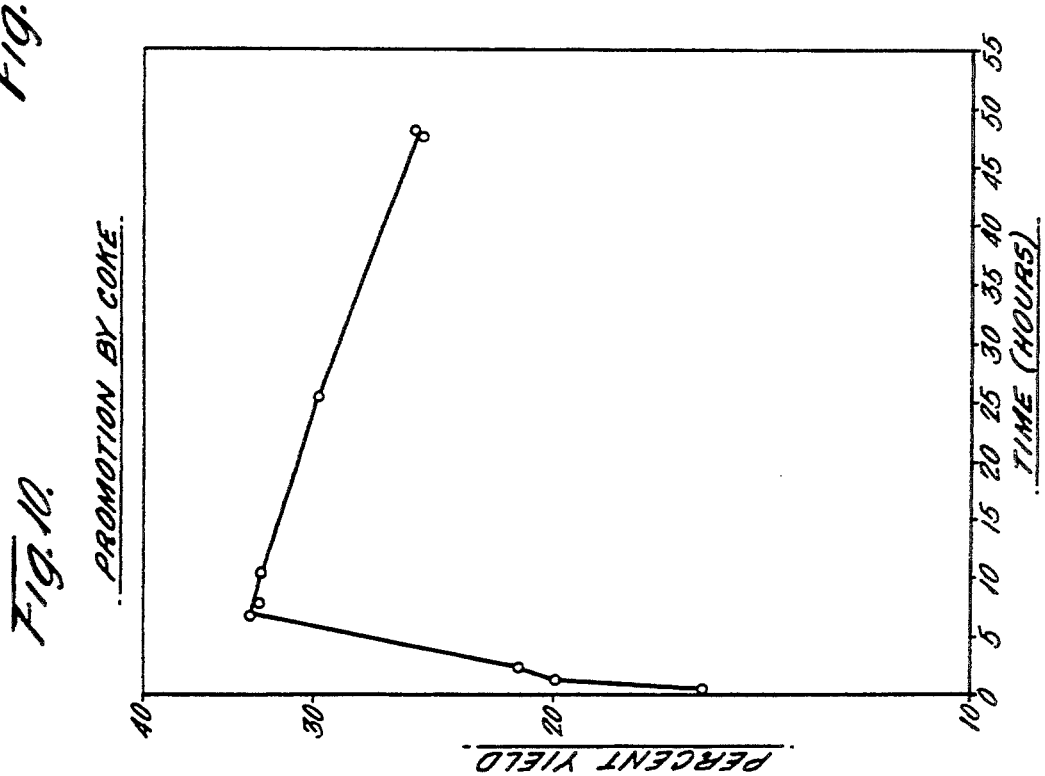
FIG. 10 shows yield of dehydrogenated product as a function of time for a catalyst containing 8.3% and 7% Cs on alumina, during its use in dehydrogenation of isobutane at 600° C. after sulfiding with dimethylsulfoxide at a hydrogen/isobutane ratio of 1.0.

For example, FIG. 10 shows an induction period to optimal catalyst activity, the delay corresponding to the buildup of a carbonaceous layer on the surface, during a fixed bed dehydrogenation reaction of isobutane. This induction period suggests that the carbonaceous deposits actively participate in the catalytic cycle.

Precarbonization can be accomplished prior to hydrogen reduction and sulfiding either with normal feed or with other compounds such as $C_3$ to $C_5$ olefins such as isobutene, for example. Coke levels of 1 to 4 weight percent on the catalyst are generally required for optimal activation of our preferred catalysts for use under severely deactivating conditions. Additional coking may lead to catalyst deactivation.

Catalysts having preferred features perform well in life tests under severely deactivating conditions of alkane dehydrogenation. Descriptions of such tests and comparative test results are shown in Examples 21 through 23.

MODIFIED PORE STRUCTURE BY LEACHING OF METAL OXIDE DEHYDROGENATION CATALYST SUPPORTS

The third embodiment as listed supra of our invention is a technique for improving formed transitional phase alumina and other similar metal oxide support phases such that the resulting treated solid oxide phase exhibits a pore size distribution in the preferred range for sulfided non-acidic nickel dehydrogenation catalysts used under severely deactivating conditions, as described supra. The resulting phase is of somewhat reduced BET surface area than the starting phase but exhibits enhanced porosity (increase pore volume) in the 50 to 200 angstrom radius range and reduced porosity (lower pore volume) in the 20–50 angstrom pore radius range, assuming cylindrical pores. The alumina phase is dispersed in hot aqueous solution containing dissolved dicarboxylic acids such as oxalic acid with stirring for a time sufficient to develop increased porosity in the solid in the 50–200 angstrom range, followed by washing and drying and calcining as described below.

Although a number of carboxylic and dicarboxylic acids may be used, succinic acid and malonic acid are preferred reagents to selectively dissolve alumina in the preferred porosity region. Oxalic acid may also be used but is not preferred. Diacids containing more than 6 carbon atoms are less favorable but may be used with some modification of time, temperature, and concentration conditions compared to preferred reagents. Any transitional phase alumina or other metal oxides which are somewhat soluble in solutions of carboxylic acids may be used. Boehmite, gamma, eta, chi, or theta phase aluminas or bauxite may be used as shaped bodies, but alpha phase alumina is sufficiently insoluble for this technique not to be useful.

After leaching, filtering, washing, and drying, the resulting solids are calcined to reduce microporosity. Useful calcination temperatures are between 700°–1100° C. for a time sufficient to reduce microporosity. Example 19 infra further illustrates the preparative method of this embodiment.

Figure 6:
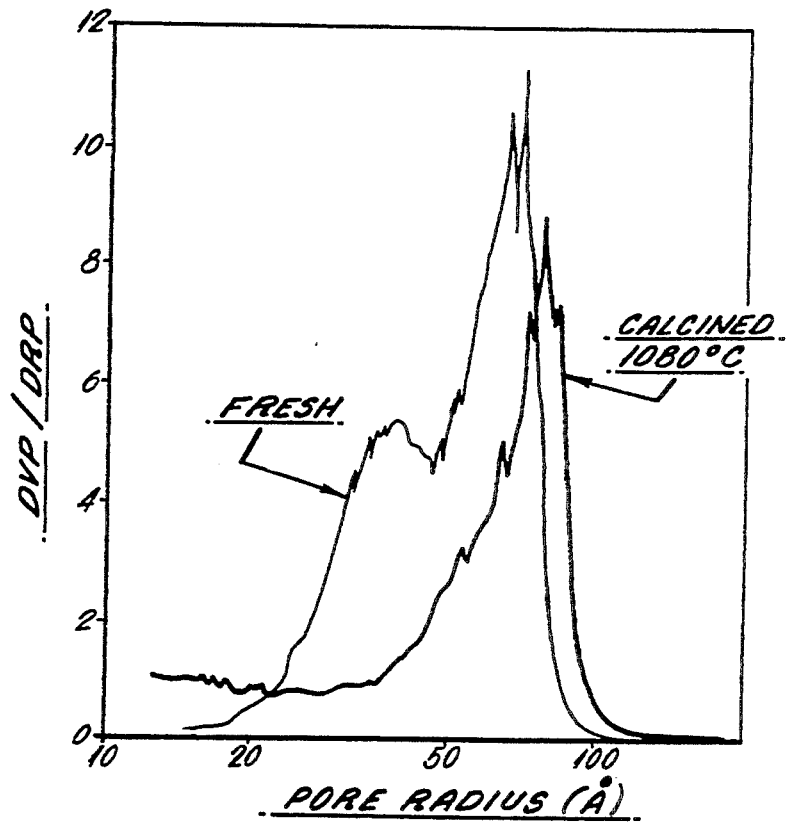
FIG. 6 shows DVP/DRP as a function of pore radius for fresh alumina and for alumina calcined at 1080° C.
Figure 7:
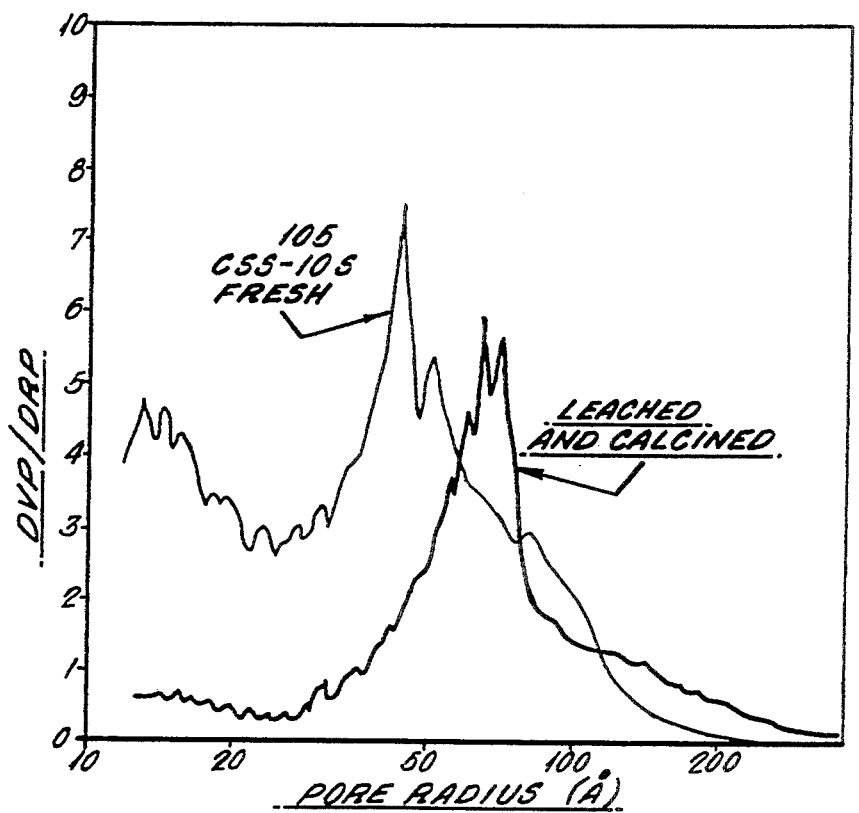
FIG. 7 shows DVP/DRP as a function of pore radius for fresh Alcoa CSS-105 alumina and for CSS-105 alumina which has been leached with hot aqueous oxalic acid and calcined.

FIGS. 6 and 7 of the drawings illustrate the effects of calcination and leaching with oxalic acid on the pore structure of the alumina support. FIG. 6 shows the alteration in pore size distribution of gamma-alumina by calcination at 1080° C. A clear decrease in the smaller pore range is observed. FIG. 7 shows the combined effect of leaching and calcination. In this case, both a decrease in the 10–50 angstrom region and an increase in the 50–200 angstrom region are clearly evident.

CATALYST CONTAINING A CARBONACEOUS LAYER BETWEEN THE SUPPORT AND THE CATALYTIC METAL

In the fourth embodiment as listed supra of our invention, described earlier, in use of sulfided nickel catalyst on non-acidic supports for dehydrogenation catalysts, carbonization can result in catalyst activation. Use of typical carbonaceous supports available commercially, as substrates for non-acidic sulfided nickel results in catalysts which show significant initial activity but decay quickly under the severely deactivating conditions described earlier. In another embodiment of the invention, a novel composition of matter is provided which has particular utility as an effective and long-lived hydrocarbon dehydrogenation catalyst under severely deactivating conditions. This composition has catalytic utility in other processes as well, including selective hydrogenation, hydrodesulfurization, and other conversion processes. The composition according to this embodiment comprises an amorphous carbonaceous layer on a porous substratum metal oxide having a particular pore size distribution. A top layer above the carbonaceous layer contains nickel plus modifier components.

The unique composition of this embodiment of the invention consists of superimposed strata on a pore modified support which have been laid down in a particular order. The substratum support consists of a porous metal oxide, preferably aluminum oxide, in the form of powder or of a formed body such as a honeycomb monolith, for example, with a particular pore size distribution. The particular pore volumes of the substratum supporting metal oxide are less than 0.1 milliliter per gram of metal oxide volume in the equivalent pore radius range of 20 to 50 angstroms, calculated from a nitrogen desorption isotherm assuming cylindrically shaped pores, and 0.25 to 1.6 milliliters per gram of metal oxide in the equivalent pore radius range of 50 to 200 angstrom pores, calculated as above. Although a number of metal oxides may be used, slightly acidic oxide surfaces that have been leached according to another embodiment of this invention to produce desirable porosity, are favored. The bulk oxide may contain minor amounts of modifier components. The substratum oxide of appropriate pore volume distribution, described above, is coated with a carbonaceous layer by any known means, preferably by thermal pyrolysis of a hydrocarbon gas, so as to produce a composite with generally 0.2 to about 6 weight percent carbon, preferably 0.4 to 4 weight percent carbon, or most preferably 1.5 to 2.5 weight percent carbon. The carbonaceous layer may also contain some hydrogen and oxygen but the hydrogen to carbon atomic ratio is preferably less than 0.2, and the oxygen to carbon ratio is preferably 0.001 to 0.16 atomic ratio. Other atomic components such as for example phosphorus, sulfur, or halogen atoms in the carbonaceous layer may be present in minor amounts, but are not preferred.

Although any suitable preparation method may be used, the amorphous carbonaceous layer may be applied to the metal oxide substratum of appropriate pore structure by thermal pyrolysis of a vaporized stream of a $C_3$ to $C_5$ alkene such as isobutene over the solid at temperatures of 700° to 800° C., for example. Additional thermal pyrolysis of the carbonized solid under a flowing nitrogen atmosphere without feeding additional hydrocarbon may be conducted to reduce the hydrogen to carbon ratio to the prescribed levels. The top stratum of the composite consists of a sulfided nickel component plus optional modifiers such that the overall nickel loading in the layered composite is in the range of 0.5 to 25 weight percent nickel, or preferably in the range of 2 to 12 weight percent nickel, or most preferably in the range of 4 to 9 weight percent nickel. The optional modifier component may be chosen from the modifiers of nickel dehydrogenation catalysts described in other embodiments of this invention. The nickel may be applied by any known technique, for example, by impregnation of the evacuated carbonized substratum to incipient wetness using a solution of nickel nitrate in acetone solvent. After solvent evaporation, the nickel-containing solid may be pyrolyzed under nitrogen at 500° C. followed by reduction under flowing hydrogen at 400° C. for 16 hours followed by sulfiding with a dimethylsulfoxide/hydrogen mixture at temperatures sufficient to decompose the dimethylsulfoxide. Prior to the sulfiding step, optional modifiers such as a cesium component or a tin component may be applied, preferably using non-aqueous solutions of reagents to impregnate the composite.

The novel compositions of this embodiment of the invention are particularly suitable catalysts for the selective dehydrogenation of dehydrogenable organic compounds under severely deactivating dehydrogenation conditions. Although the invention is not to be limited by any theory of operation, catalysts of our novel compositions feature a large number of sites of organometal species (interface sites between nickel and hydrogenatable organic moieties) which we believe to be the active site in the working catalyst (resulting in high activity) but pocketed in a pore structure which promotes a low deactivation rate (resulting in long life on-stream).

Compositions consisting of nickel deposited onto a carbonaceous support followed by reduction and sulfiding differ from our novel compositions in that pure carbon-type supports do not typically contain the large pore structures appropriate for long life. These known catalysts have high initial activities, but decay quickly. Our novel catalysts of this embodiment, on the other hand, have the appropriate carbon-nickel interaction for high activity yet maintain high activity substantially longer than nickel on uniform carbon supports, particularly under severely deactivating dehydrogenation conditions.

CATALYST FOR SELECTIVE HYDROGEN OXIDATION

In the fifth embodiment as listed supra, the invention relates to the preparation and use of a catalyst which selectively promotes hydrogen combustion while minimizing combustion of desirable hydrocarbon. The catalyst can be used in connection with the dehydrogenation processes disclosed herein, as well as in other processes involving selective oxidation of hydrogen such as those disclosed in U.S. Pat. Nos. 4,435,607 and 4,788,371.

The catalyst used in this embodiment of this invention is a metal phosphate, preferable a phosphate of a metal in Group IVb or Vb and more preferably a phosphate of tin. These compounds are known in the prior art; see for example U.S. Pat. No. 4,252,680. Other Group IVb or Vb metals may be used, for example, bismuth.

To use the catalysts of this embodiment, a mixture of hydrogen and hydrocarbons is contacted with the catalyst and an oxygen-containing gas at hydrogen oxidation conditions, to allow hydrogen and oxygen to react, and a reaction product mixture containing water in the form of steam and unreacted hydrocarbons is removed from the reaction zone. Alternatively, pure hydrogen or a dilute hydrogen stream in an inert carrier may be used. Preferred conditions are temperatures in the range from 430° to 600° C., pressures in the range from 0 to 50 psig and space velocities in the range from 5,000 $h^{-1}$ to 40,000 $h^{-1}$. Preferably, the amount of oxygen used is in the range from 0.5 to 1.1 moles of oxygen per mole of hydrogen burned.

Figure 12:
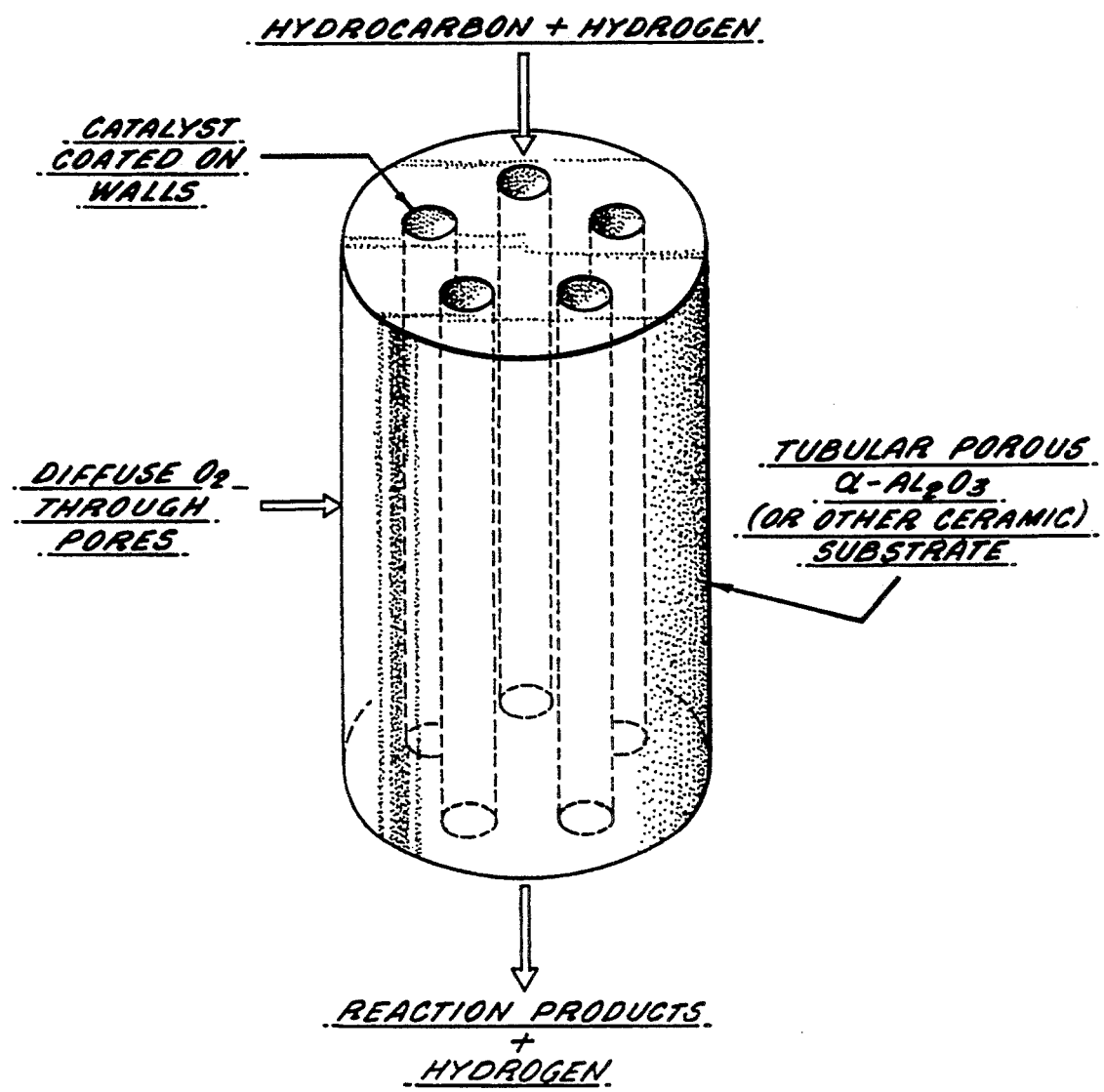
FIG. 12 shows a reactor which may be used in selective oxidation of hydrogen.

The catalyst used may be in the form of a bed of granular solids. Alternatively, it may be coated on a porous honeycomb monolithic support as shown in FIG. 12 of the drawings. Use of the catalyst on the structure of FIG. 12 prevents bulk mixing of oxygen and hydrocarbons and hydrogen except at the interface over the selective catalyst. To mitigate migration of tin compounds off of the catalyst at high temperature, a pretreatment step may be performed with hydrogen at about 600° C. as a final step of catalyst preparation to remove excessive amount of tin prior to use.

In addition to Group IVB or Group VB compounds, minor amounts of iron, manganese, or chromium salts may be added to the catalyst during the gelling stage, as combustion initiators for low temperature service, preferably when the catalyst is to be used below about 500° C. The pressure of the oxygen stream is slightly higher than that of the hydrogen/hydrocarbon stream, preferably within the range of 1.1 to 2 times higher.

The monolith structure of FIG. 12 can also be used in the catalytic dehydrogenation processes disclosed herein, the dehydrogenation catalyst being coated on the support in the manner illustrated in FIG. 12 for the oxidation catalyst.

Example 23 infra illustrates this embodiment of the invention.

MULTI-STEP PROCESS FOR DEHYDROGENATION USING PARTICULAR CATALYSTS FOR THE DEHYDROGENATION SECTION

This embodiment is a process for dehydrogenation of dehydrogenatable hydrocarbons using a combination of the general process scheme described in an earlier embodiment along with the dehydrogenation catalysts of this invention described in other embodiments. Any hydrogen combustion catalyst may be used of sufficient activity and selectivity. A narrower range of process operating conditions than in the more general embodiment results in favorable process economics and good catalyst performance. The dehydrogenation catalysts used in this embodiment are sulfided nickel on non-acidic pore-modified supports and the operating conditions in this embodiment are as described in other embodiements, with the exceptions noted below.

Once the catalysts have been installed, sulfided and activated in a reactor, as previously described herein, hydrocarbon feed is introduced along with hydrogen as previously described. Surprisingly, there is an optimal ratio of hydrogen to hydrocarbon feed for best catalyst performance. Catalyst performance is measured by computing the ratio of initial dehydrogenation rate to average deactivation rate as a function of hydrogen to hydrocarbon ratio at a given operating temperature, say 600 degrees C., operation. The greater this merit ratio, the better the performance. When the feed is isobutane, the optimum ratio of hydrogen to isobutane is between about 0.3 to 0.5, as shown in FIG. 13 of the drawings. Other hydrocarbon feed components show optima differing slightly from that of isobutane.

Under typical operation at these optimal conditions, the catalysts described herein will eventually lose activity. We believe that a reasonable cycle length is governed by the time it takes to build up 10-15% weight coke as measured by LECO carbon analysis, that is, the time to just fill the large pores of the preferred catalyst formulation with coke or slightly lesser time. Regeneration can then be easily accomplished by feeding air or diluted air or oxygen over the catalyst at 400° to 600° C., preferably 440° to 490° C., for a time sufficient to combust a portion of, but not all of the coke. Optimally, 0.5-1.0 weight percent coke may be left on the catalyst after the regeneration cycle, but values as low as 0.02 weight percent may be tolerated. Typical regeneration times under air or oxygen at 600° C. are 0.5 to 6 hours, but the exact time depends on the level of carbon burn-off to be achieved and on the feed rate of oxygen-containing gas. Catalysts containing a barrier layer generally require a lower temperature, for example, less than about 500° C., for regeneration, than that required for catalysts not containing a barrier layer. After burnoff, the catalyst is reduced and resulfided and optionally further activated by allowing coke to build to optimal levels prior to resumption of the dehydrogenation step. The sulfiding and reduction may be done concurrently with the early part of the subsequent dehydrogenation step.

DETAILED DESCRIPTION OF MULTI-STEP PROCESS

The multi-step process of one embodiment of the invention will be further described with reference to FIG. 1, which is a schematic diagram of a typical process flow according to the invention:

Butanes and hydrogen are introduced into zoned adiabatic reactor 10 through line 12, and contacted in reactor 10 with a bed 14 of granular dehydrogenation catalyst. Butanes in the feed are dehydrogenated to form butenes and additional hydrogen, which pass upwardly together with unreacted butanes into bed 16 of granular catalyst for the selective oxidation of hydrogen to water. Because of the endothermic nature of the dehydrogenation reaction, the reaction mixture undergoes a reduction in temperature between the point of entry into the bed 14 and the point of entry from bed 14 into bed 16. In bed 16, a portion of the hydrogen is selectively oxidized, leaving the hydrocarbons mainly unoxidized, and generating heat which raises the temperature of the reaction mixture to prepare the mixture for the second dehydrogenation catalyst bed 18. In bed 18, previously unreacted butane is dehydrogenated to form additional butene and hydrogen, the reaction mixture undergoing another reduction in temperature in the process. The reaction product mixture passes from bed 18 into bed 20, wherein a portion of the hydrogen produced in bed 18 is selectively oxidized to form water and generate heat which prepares the reaction mixture for the third dehydrogenation catalyst bed 22. In bed 22, previously unreacted butanes are dehydrogenated to form additional hydrogen and butenes product. The reaction product mixture is removed from reaction vessel 10 through line 24, then is passed through indirect heat exchange with fresh and recycle butane feed introduced into heat exchanger 26 through line 28. The product mixture is then introduced into condenser 29 wherein water is condensed from the mixture and removed through line 30. The uncondensed product mixture is then passed into hydrogen-selective membrane separator 32 through line 34. Butane/butene product is removed through line 36 to butane/butene separation not shown. Net hydrogen production from the process is removed through line 38, and hydrogen recycle is passed through lines 40 and 12 into reactor 10. Heated fresh and recycle butane feed is introduced into reactor 10 through lines 42 and 12.

Catalysts used for dehydrogenation according to the embodiments of the invention, require sulfidation for optimum performance. Sulfidation may be done prior to loading catalyst in the reactor and/or may be done by adding a sulfur-containing material to the reactants, as through line 44 in FIG. 1, or other suitable point of introduction. In some cases at least, even though the catalysts are presulfided, additional sulfur is needed in order to maintain catalyst selectivity.

Steam may optionally be employed in the process according to the invention, through line 44 or at other suitable point of introduction.

MULTI STEP PROCESS FOR DEHYDROGENATION USING PARTICULAR CATALYSTS FOR THE DEHYDROGENATION SECTION AND PARTICULAR CATALYSTS FOR THE HYDROGEN COMBUSTION SECTION

In this seventh embodiment listed supra, sulfided nickel on non-acidic support or sulfided nickel and carbon on a large pore alumina support is used as dehydrogenation catalyst, and tin phosphate, for example, is used as selective hydrogen combustion catalyst in the multiple step process, all as previously described.

EXAMPLES OF CATALYTIC DEHYDROGENATION WITH PARTICULAR CATALYSTS

The invention will be further described in connection with the following examples:

In Examples 1 through 6, catalysts according to the invention containing zeolitic supports were tested for dehydrogenation of normal butane and compared to the performance of the catalyst of U.S. Pat. No. 4,727,216 (prepared according to the patent directions) in the presence of hydrogen after sulfiding.

EXAMPLE 1

The catalyst according to U.S. Pat. No. 4,727,216 was prepared as follows: ELZ-L Mol Sieve manufactured by Union Carbide Corporation, 1/16" extrudate, was ground and sieved to 18/35 mesh. The zeolite was exchanged three times with hot 0.21 molar barium nitrate solution, with calcination between exchanges washed with hot deionized water, and dried at 125° C. The dried catalyst was calcined in a muffle at 590° C. for 2.0 hours. The zeolite was impregnated to incipient wetness with a solution of tetraamine platinum nitrate and dried in a 125° C. oven. It was calcined in a muffle programmed to heat at 3 C/minute to 260° C. and hold at 260° C. for 2.0 hours. The catalyst was then transferred to a tube furnace and heated in flowing hydrogen at 482° C. for 1.0 hour. The catalyst was impregnated by incipient wetness with a pentane solution of tributyl tin chloride, after which the solvent was allowed to weather off at room temperature. It was then heated in flowing air at 482° C. for 1.2 hours, followed by flowing hydrogen at 482° C. for 2.0 hours. After the hydrogen treatment, the catalyst was treated with 3 percent hydrogen sulfide in hydrogen at 482° C. for 15 minutes. Further sulfiding was conducted in the reactor. The finished catalyst was analyzed by atomic adsorption and found to contain 0.99% Pt, 0.45% Sn and 7.3% Ba after appropriate dissolution. Analysis for sulfur was inconclusive.

EXAMPLE 2

A Ni—Sn—Ba L zeolite catalyst according to the invention was prepared as follows. A portion of ELZ-L Mol Sieve, 18/35 mesh, was exchanged twice with hot 0.23 molar barium nitrate solution, dried at 125° C. and calcined in a muffle at 590° C. for 2.0 hours. The zeolite was impregnated by incipient wetness with a solution of nickel nitrate hexahydrate, dried at 125° C. and heated in a tube furnace in flowing air at 260° C. for 1.5 hours, followed by treatment with flowing hydrogen at 420°-550° C. for 1.5 hours. The catalyst was impregnated to incipient wetness with a pentane solution of tributyl tin chloride, after which the solvent was allowed to weather off. The catalyst was then calcined at 560° C. in flowing air for 1.0 hour, and heated in flowing hydrogen sulfide/hydrogen (5% $H_2S$) at 482° C. for 1.0 hour. The finished catalyst was analyzed by atomic absorption to contain 0 23% Ni, 0.56% Sn, and 6.04% Ba after appropriate dissolution.

EXAMPLE 3

A Ni—Sn—Na—S mordenite catalyst according to the invention was prepared as follows. Hydrogen mordenite (Norton H-Zeolon) was exchanged successively with 0.05M NaOH at 70° C. and finally with 0.75M NaOH at 65° C. The exchanged mordenite was dried at 125° C. and slurried with enough colloidal silica (Nyacol 30% $SiO_2$ manufactured by PQ Corp.) to give 18 percent silica on the finished catalyst. After drying at 125° C., the bound mordenite was ground and sieved to 18/35 mesh. A portion of the mordenite granules was impregnated to incipient wetness with a solution of nickel nitrate hexahydrate and dried at 125° C. The catalyst was calcined at 590° C. for 2.0 hours, followed by treatment with flowing hydrogen at 482° C. for 1.0 hour. The reduced catalyst was exposed to air at room temperature, and impregnated with a pentane solution of tributyl tin chloride. The solvent was allowed to weather off at room temperature, after which the catalyst was calcined at 482° C. for 1.0 hour. A portion of the calcined catalyst was treated with a flowing stream of 5 percent hydrogen sulfide in hydrogen at 482° C. for 1.0 hour. Analysis of the finished catalyst indicated it contained 0.96% Ni, 1.90% Sn, and 3.75% Na. Prior to testing, this catalyst was sulfided further by passing 500 ppm $H_2S$ in $H_2$ over it at about 450° C. for 0.5 hour followed by pure hydrogen for 15 minutes.

EXAMPLE 4

The catalyst of Example 3 was given a further sulfiding and reduction treatment in the reactor by passing 500 ppm $H_2S$ in hydrogen over it at about 590° C. for 45 minutes followed by pure hydrogen for fifteen minutes.

EXAMPLE 5

A portion of the sodium-exchanged mordenite granules from the preparation of Example 3 was exchanged with a hot 0.034M solution of nickel nitrate hexahydrate and washed with hot deionized water. The impregnated catalyst was dried overnight at 95° C. and later impregnated by incipient wetness with a solution of copper(II) nitrate hemipentahydrate. After drying at 125° C., the impregnated catalyst was heated in flowing hydrogen at 450° C. for 2.0 hours. Analysis of the catalyst indicated it contained 1.40% Ni and 3.75% Na. Prior to testing, the catalyst was reduced by flowing hydrogen over it while the temperature was raised at 5°/min up to 590° where it was held for 10 minutes prior to switching to the test feed solution.

EXAMPLE 6

A portion of the catalyst prepared according to Example 5 was sulfided followed by pure hydrogen treatement in the reactor by the same procedure described above for the preparation of the catalyst of Example 4.

The tests on the above catalysts of Examples 1 through 6 were conducted in an isothermal downflow packed bed, quartz, computer-supervised reactor equipped with on-line multidimensional GC analytical capability and with a quadrupole mass spectrometer which could sample the full stream composition and which featured low ionization voltage capability to determine molecular ions. The GC system was calibrated against commercial mixtures of the expected hydrocarbon products and against internal compositions generated by mass flow controllers which in turn had been calibrated against a wet test meter certified traceable to the National Bureau of Standards. The continuously operating MS detector was used to monitor compositional trend changes between samples taken for on-line GC analyses. The catalysts were each prereduced under flowing hydrogen followed by sulfiding with 500 ppm $H_2S$ in $H_2$ (off-line) for one hour at up to 590° C. followed by further treatment with pure hydrogen after which time they were brought to reaction temperature and the feed changed to 6:1 hydrogen to butane at the specified GHSV. Internal temperature was monitored by a thermocouple inserted into the bottom third of the catalyst bed; pressure was controlled by automatic feedback loop back pressure regulator at 39+2 psig and flow by a combination of mass flow controllers and an HPLC metering pump for liquid butane. Normal butane was vaporized and mixed with hydrogen prior to the reactor. No data were taken for one hour to allow steady state to be achieved, then data were taken at 2 hour intervals thereafter for at least 12 hours. No further sulfur was added in these tests after the initial treatment of the catalyst.

The results of these tests are summarized in Table I. A few runs showed higher conversions than equilibrium conversion due to a contribution of unselective conversion to generate hydrogenolysis products such as methane, ethane, propane, propene, or ethene, grouped under the heading $C_{3-}$ in the table. Thus, high conversions are undesirable when due to poor selectivity. No butadiene was detected in any run in other than trace quantities. Isobutane yield, resulting from isomerization of the normal butane feed, is not reported, but is minor. The preferred catalysts for use according to the invention minimize isomerization.

EXAMPLES OF NICKEL-CHROMIUM DEHYDROGENATION CATALYST COMPOSITIONS

Catalysts of the type described supra containing nickel and chromium were prepared and compared to controls in which one of the essential components was missing, either the chromium, the nickel or the sulfiding. Testing was conducted in a manner described previously in a computer supervisory controlled quartz, packed-bed reactor with on-line analytical capability after sulfiding with 500 ppm $H_2S$ in $H_2$ followed by pure hydrogen treatment to remove excess $H_2S$.

All catalysts described below were sulfided and re-reduced just before use in the test reactor system with 500 ppm $H_2S/H_2$ for one hour at 450°–590° C. followed by $H_2$ treatment at 590° C.

The silica used was PQ CS-1231, Lot No. 994-8601, 335 $m^2/g$ pore volume +1.25 ml/g, 18/35 mesh, dried at 125° C.

EXAMPLE 7

Nickel Oxide on Chromia/Silica 1.93 g. chromium trioxide, $CrO_3$, was dissolved in deionized water to give a 50 ml solution. This solution was used to impregnate 50.2 g. of silica to incipient

TABLE I

| | COMPARISON OF CATALYST PERFORMANCE FOR n-BUTANE DEHYDROGENATION IN THE PRESENCE OF HYDROGEN ($C_4$ GHSV = 500 h, $H_2$ GHSV = 3000 h, Packed Bed Reactor) | | | | | |
|---|---|---|---|---|---|---|
| CATALYST | TEMP (°C.) | TIME (HRS) | $C_4$ CONV. (MOL %) | SELEC. $C_4=$ (C MOL %) | SELEC. $C_3-$ (C MOL %) | YIELD $C_4=$ (MOL %) |
| A. Example 1 Pt/Sn/Ba-L zeol/S | 590 | 1–12 | 46.9 ± 1.9 | 38.5 ± 1.2 | 50.2 ± 1.2 | 18.1 |
| B. Example 2 Ni/Sn/Ba-L zeol/S | 584 | 1–12 | 7.6 ± 1.3 | 58.1 ± 1.1 | 31.2 ± 0.5 | 2.4 |
| C. Example 3 Ni/Sa/mordenite/S (low severity S) (0.97 wt % Ni, 1.90 wt % Sn, VF) | 592 | 1 3 12 | 8.2 9 10 | 54.8 68.8 62 | 33.7 31.2 38 | 6.2 6.2 |
| D. Example 4 Ni/Sn/mordenite/S (high severity S) | 590 | 1 6 12 | 6.0 7.8 9.2 | 64.5 61.8 61.2 | 35.5 38.2 38.8 | 3.8 4.8 5.6 |
| E. Example 5 Ni/Cu/mordenite not sulfided | 628 613 602 587 560 | 1 3 12 1 1 | 100 86.1 66.0 66.4 64.6 | 0 0 3.2 4.2 1.5 | 100 100 96.8 95.8 98.5 | 0 0 2.1 2.8 1 |
| F. Example 6 Ni/Cu/mordenite/S (high nickel) | 591 | 1 3 6 9 12 | 14.3 23.0 25.9 27.0 28.6 | 61.2 66.3 38.0 52.2 47.5 | 31.2 33.7 42.0 47.8 43.8 | 8.7 15.2 15.0 14.1 13.6 |

Comparing the first two lines of the table, one finds that at equivalent molar loading in Ba-L zeolite, nickel was less active but more selective than Pt after $H_2S$ sulfiding. The Pt catalyst was of the composition of the 216 patent supra. Without sulfiding, the Ni/Cu alloy catalyst severely destroyed butane to hydrogenolysis. The selectivity performance of the Ni/Cu composition shown decayed somewhat with time, the yield of butenes going through a maximum. We believe this was due to the loss of sulfur from the catalyst with the time on-stream and that this catalyst would fare better in a reactor in which sulfur was continuously fed or after sulfiding with the preferred reagents.

wetness. Dried overnight in 125° C. oven. A portion of the catalyst was put in a bottle and saved. The remainder was heated in flowing air at 540° C. for one hour. 28.7 g. of the calcined catalyst were impregnated with 32 ml of aqueous solution containing 4.22 g. nickel nitrate hexahydrate. Dried for two days in 125° C. oven, and heated in flowing air at 540° C. for several hours. Cooled to room temperature. Heated in flowing hydrogen at 450° C. for 2 hours. Expected 2% Cr, 3% Ni Found 1.83% Cr, 2.54% Ni

EXAMPLE 8

Nickel Oxide on Chromia/Silica

A portion of the chromia/silica produced as described below was heated in flowing air at 540° C. for one hour. 20.4 g. of the chromia/silica were impregnated with 24 ml of an aqueous solution containing 3.01 g. of nickel nitrate hexahydrate. Dried overnight in 125° C. oven. Heated in flowing hydrogen to 450° C. and held at 450° C. in flowing hydrogen for 2 hours. Expected 1.0% Cr, 2.9% Ni. Found 1.04% Cr, 2.64% Ni.

EXAMPLE 9

Chromia/Silica 50 g. of silica were impregnated with 53 ml of aqueous solution containing 1.03 g. chromium trioxide. Dried overnight in 125° C. oven.

EXAMPLE 10

Ni+Sn on Chromia/Silica 16.8 g. of the $H_2$-treated Ni/Cr/silica prepared as described above, were impregnated with 20 ml of a benzene solution containing 2.47 g. of tetrabutyl tin, Aldrich.

The impregnated catalyst was allowed to stand wet for three days, after which the benzene was allowed to weather off in the hood. The catalyst was heated slowly in flowing nitrogen to 300° C. and held at 300° C. for one hour, then cooled, the flow changed to hydrogen, and heated to 450° C. The catalyst was then held at 450° C. in flowing hydrogen for 1.5 hours. Expected 5% Sn. Found 3.33% Sn.

EXAMPLE 11

Chromia/Silica 30 g. of silica were impregnated with 32 ml of aqueous solution containing 2.5 g. of chromium trioxide, then dried overnight in 125° C. oven, heated in flowing air at 540° C. for 2 hours, and cooled to room temperature. The flow was changed to hydrogen and the catalyst heated slowly to 450° C., then heated in flowing hydrogen at 450° C. for one hour.

EXAMPLE 12

Highly Dispersed Nickel on Silica 33.4 g. of silica were impregnated with 70 ml of dry acetone solution containing 4.34 g. of nickel nitrate hexahydrate. The acetone was removed under vacuum. The catalyst was heated in flowing hydrogen to 450° C. and held at 450° C. for one hour. Expected 2.6% Ni. Found 2.16% Ni.

Results of normal butane dehydrogenation appear in Table II.

TABLE II

| | COMPARISON OF CATALYST PERFORMANCE FOR n-BUTANE DEHYDROGENATION IN THE PRESENCE OF HYDROGEN ($C_4$ GHSV = 500 $h^{-1}$, $H_2$ GHSV = 3000 $h^{-1}$, PACKED BED REACTOR, 591 ± 1° C., P = 31 PSIG) | | | | | |
|---|---|---|---|---|---|---|
| | CATALYST | ON STREAM TIME (Hrs.) | $C_4$ CONV. (MOL %) | SELEC. $C_{4=}$ (C MOL %) | YIELD $C_{4=}$ (MOL %) | $CH_4/C_2H_6$ (In $C_3$-Prods) |
| 1. | 2.16% Ni/$SiO_2$/S Example 12 | 1 | 37.6 | 48.0 | 18.1 | 3.6 |
| | | 3 | 43.8 | 39.8 | 17.4 | 6.3 |
| | | 6 | 49.0 | 18.3 | 9.0 | 5.3 |
| | | 9 | 51.6 | 19.3 | 10.0 | 16.5 |
| | | 12 | 58.2 | 19.0 | 11.0 | 17.8 |
| 2. | 1.94% Cr/$SiO_2$/S | 1 | 41.4 | 32.7 | 13.5 | |
| | | 3 | 25.1 | 58.5 | 14.6 | |
| | | 6 | 30.9 | 58.2 | 18.0 | |
| | | 9 | 36.4 | 58.3 | 21.2 | |
| | | 12 | 24.7 | 59.0 | 14.6 | |
| | | 15 | 17.8 | 61.0 | 10.9 | |
| | | 18 | 26.0 | 58.9 | 15.3 | |
| | | 21 | 37.4 | 32.5 | 12.1 | |
| | | 24 | 36.5 | 32.4 | 11.8 | |
| 3. | 2.64% Ni/1.04% Cr/$SiO_2$/No S | 1 | 100 | 0 | 0 | Infinity |
| 4A. | 2.64% Ni/1.04% Cr/$SiO_2$/S Example 8 | 1 | 26.5 | 32.1 | 8.5 | 1.1 |
| | | 3 | 32.2 | 58.5 | 18.8 | 1.2 |
| | | 6 | 13.2 | 63.6 | 8.4 | 0.5 |
| | | 9 | 27.1 | 62.3 | 16.9 | 0.4 |
| | | 12 | 35.1 | 59.3 | 20.8 | 1.2 |
| 4B. | RESULFIDE | 1 | 25.2 | 50.3 | 12.7 | 1.2 |
| | | 3 | 28.6 | 60.6 | 17.3 | 1.2 |
| | | 6 | 17.5 | 64.8 | 11.3 | 0.3 |
| | | 9 | 27.8 | 63.2 | 17.6 | 0.5 |
| | | 12 | 28.4 | 63.1 | 17.9 | 0.4 |
| 5. | 2.6% Ni 3.3% Sn/1.0% Cr/$SiO_2$/S Example 10 | 1 | 18.9 | 31.0 | 5.9 | 1.2 |
| | | 3 | 17.1 | 30.9 | 5.3 | 1.2 |
| | | 6 | 19.1 | — | — | — |
| | | 9 | 22.4 | 31.0 | 7.0 | 1.2 |
| | | 12 | 19.8 | 30.9 | 6.1 | 1.2 |
| 6. | 1.8% Cr/2.5Ni/ $SiO_2$/S Example 7 | 1 | 17.6 | 0 | 0 | |
| | | 3 | 22.9 | 61.2 | 14.0 | |
| | | 6 | 15.0 | 61.9 | 9.3 | |
| | | 9 | 27.4 | 59.4 | 16.3 | |
| | | 12 | 21.7 | 59.0 | 12.8 | |
| | | 15 | 27.7 | 57.5 | 15.9 | |
| | | 18 | 24.8 | 58.4 | 14.5 | |
| | | 21 | 25.8 | 57.9 | 14.9 | |
| | | 24 | 53.6 | 58.2 | 31.2 | |

No butadiene was detected in any of the runs of Table II.

The data in Table II show the relatively rapid decline in selectivity and yield with increasing time on-stream over a silica-supported catalyst after initial sulfiding; no sulfur was cofed with butane and hydrogen. The increase in $CH_4/CH_2H_6$ ratio (Table II) correlates with desorption of sulfur as $H_2S$ with time on-stream.

Chromiated silica is represented by entry 2 of Table II. Yield improved over 9 hours, then declined over this catalyst; selectivity declined after about 18 hours as shown in Table II, entry 2.

Without sulfiding, only hydrogenolysis products ($CH_4$) were observed from a 2.6% Ni/1% Cr/$SiO_2$ catalyst (entry 3 of Table II). Presulfiding resulted in low methane yields (low $CH_4/C_2H_4$) and high selectivities and yields (entries 4A,B of Table II). These good results were sustained much longer than those of the Ni/$SiO_2$/S catalyst which contained no chromium. When selectivity began to drop slightly after 12 hours on-stream, resulfiding restored selectivity after an induction period. Low $CH_4/C_2H_6$ ratios were observed after resulfiding (entry 4B of Table II).

Another example of superior yield and selectivity of the Ni/Cr/$Si_2$/S-type catalysts is entry 6 of Table II.

NOVEL NICKEL CATALYSTS ON NON-ACIDIC FORMS OF ZEOLITE L

In another set of examples, novel nickel-based catalysts, optionally alloyed with tin or indium, are supported on non-acidic forms of zeolite L such as exhaustively barium-exchanged L zeolite. The catalysts exhibit good selectivity for production of monoolefins without generating much coke or diolefins and with little hydrogenolysis product (e.g., methane) production under conditions in which hydrogen is cofed along with normal butane at high temperature over the catalyst.

EXAMPLE 13

Catalyst was prepared as follows:

Exchanges: 53.2 g. zeolite L (Union Carbide Lot #11842-31, 16" extrudate, ground and sieved to 18/35 mesh) granules are immersed in 500 ml of 0.5M barium chloride solution at 70° C. with gentle stirring for 30 minutes. The solution was decanted and the zeolite washed three times in hot deionized water. The zeolite was dried in 125° C. oven and heated in a muffle furnace programmed to heat at 9° C./minute to 593° C. and hold for two hours. This procedure was repeated three more times using 250 ml quantities of 0.5M barium chloride solution. The product was labeled as Sample A.

Impregnation: 5.0 g. of nickel nitrate hexahydrate were dissolved in dry acetone to give 20 ml of solution. This solution was used to impregnate 39.8 g. of the above zeolite by incipient wetness. The acetone was allowed to weather off in a hood, after which it was dried in a 125° C. oven and calcined in a muffle at 400° C. for one hour. Labeled as Sample B.

Impregnation: Approximately half of Sample B, 18.3 g., was impregnated with 10 ml of a benzene solution containing 2.72 g. of tetrabutyltin. The impregnated zeolite was allowed to stand wet overnight, after which it was loaded into a tube furnace and heated slowly in flowing nitrogen to 300° C. The heating continued at 300° C. in flowing nitrogen for 105 minutes. Labeled as Sample C.

Table III below illustrates the outstanding performance characteristics of Ni—Sn—Ba—L catalysts for n-butane dehydrogenation under conditions in which hydrogen is cofed along with the alkane.

All catalysts in Table III were presulfided in-situ prior to testing with 500 ppm $H_2S/H_2$ for one hour between 450°–590° C. followed by $H_2$ reduction.

TABLE III

COMPARISON OF CATALYST PERFORMANCE FOR n-BUTANE DEHYDROGENATION IN THE PRESENCE OF HYDROGEN ($C_4$ GHSV = 500 $h^1$, $H_2$ GHSV = 3000 $h^1$, PACKED BED REACTOR, 591 ± 1° C., P = 31±2 PSIG)

| CATALYST | ON STREAM TIME (Hrs.) | $C_4$ CONV. (MOL %) | SELEC. $C_4=$ (C MOL %) | YIELD $C_4=$ (MOL %) | $CH_4/C_2H_6$ (In $C_3$-Prods) |
|---|---|---|---|---|---|
| Pt/Sn/Ba-L zeol/S | 1–12 | 46.9 ± 1.9 | 38.5 ± 2.1 | | |
| 2.16% Ni/$SiO_2$/S | 1 | 37.6 | 48.0 | 18.1 | 3.6 |
| | 3 | 43.8 | 39.0 | 17.4 | 6.3 |
| | 6 | 49.0 | 18.3 | 9.0 | .AC |

Dumping file f:
prod
cwuid
05440038.0C

Dumping file f:
prod
cwuid
05439998.0C

Dumping file f:
prod
cwuid
05439910.AC

Dumping file f:
prod
cwuid
05439676.0C

Dumping file f:
prod
cwuid
05440671.0C

Dumping file f:
prod
cwuid
05439863.0C

TABLE III-continued

COMPARISON OF CATALYST PERFORMANCE FOR n-BUTANE DEHYDROGENATION IN THE PRESENCE OF HYDROGEN ($C_4$ GHSV = 500 $h^1$, $H_2$ GHSV = 3000 $h^1$, PACKED BED REACTOR, 591 ± 1° C., P = 31±2 PSIG)

| CATALYST | ON STREAM TIME (Hrs.) | $C_4$ CONV. (MOL %) | SELEC. $C_4$= (C MOL %) | YIELD $C_4$= (MOL %) | $CH_4/C_2H_6$ (In $C_3$-Prods) |
|---|---|---|---|---|---|
| Dumping file f: prod cwuid 05439747.0C | | | | | |
| Dumping file f: prod cwuid 05439997.0C | | | | | |
| Dumping file f: prod cwuid 05439954.AC | | | | | |
| Dumping file f: prod cwuid 05439251.AC | | | | | |
| Dumping file g: prod table 05439640.02 | | | | | |
| Dumping file g: prod table 05440477.01 | | | | | |
| Dumping file g: prod table 05440730.01 | | | | | |
| Dumping file f: prod cwuid 05437816.02 | | | | | |
| Dumping file g: prod table 05440716.01 | | | | | |
| Dumping file g: prod table 05439954.01 | | | | | |
| Dumping file g: prod table 05439896.01 | | | | | |
| Dumping file g: prod table 05439887.01 | | | | | |
| Dumping file g: prod table 05439859.01 1.1 | | | | | |
| | 6 | 23.3 | 70.4 | 16.4 | 0.3 |
| | 9 | 32.8 | 69.2 | 22.7 | 0.5 |
| | 12 | 37.1 | 68.8 | 25.5 | 0.4 |
| Overnight/He/200° | 1 | 42.6 | 48.5 | 20.6 | 1.2 |
| | 3 | 30.9 | 56.3 | 17.4 | 0.6 |
| | 6 | 31.7 | 55.8 | 17.7 | 0.8 |
| | 9 | 33.4 | 54.9 | 18.3 | 0.7 |
| | 15 | 45.5 | 61.5 | 28.0 | 0.5 |
| | 12 | 39.2 | 54.4 | 21.3 | 0.8 |
| | 18 | 40.5 | 54.0 | 21.9 | 0.8 |
| | 21 | 41.0 | 54.5 | 22.3 | 0.7 |
| | 24 | 37.5 | 54.0 | 20.3 | 0.8 |

TABLE III-continued

COMPARISON OF CATALYST PERFORMANCE FOR n-BUTANE DEHYDROGENATION
IN THE PRESENCE OF HYDROGEN ($C_4$ GHSV = 500 $h^1$, $H_2$ GHSV = 3000 $h^1$,
PACKED BED REACTOR, 591 ± 1° C., P = 31±2 PSIG)

| CATALYST | ON STREAM TIME (Hrs.) | $C_4$ CONV. (MOL %) | SELEC. $C_4=$ (C MOL %) | YIELD $C_4=$ (MOL %) | $CH_4/C_2H_6$ (In $C_3$-Prods) |
|---|---|---|---|---|---|
| Resulfide | 1 | 36.4 | 48.1 | 17.5 | 1.1 |
| | 6 | 31.4 | 66.3 | 20.8 | 1.3 |
| | 12 | 29.4 | 69.4 | 20.4 | 0.4 |
| | 15 | 43.0 | 68.0 | 29.3 | 0.4 |
| | 18 | 43.6 | 68.8 | 30.0 | 0.3 |
| | 21 | 44.9 | 68.2 | 30.6 | 0.4 |
| | 24 | 32.8 | 55.3 | 18.2 | 0.6 |
| 2.4% Ni/2.7% Cu/K-MORDEN/S (3.68% K) | 3-A | 9.2 | 0 | 0 | 0.6 |
| | 6 | 27.5 | 0 | 0 | 0.02 |
| | 9 | 12.5 | 0 | 0 | 0.4 |
| | 12 | 25.8 | 0 | 0 | 0.02 |
| | 15 | 13.8 | 30.2 | 4.2 | 0.5 |
| | 18 | 20.4 | 48.8 | 10.0 | 0.3 |
| Resulfide | 3A | 13.9 | 0 | 0 | 0.4 |
| | 6 | 12.6 | 0 | 0 | 0.3 |
| | 9 | 13.2 | 0 | 0 | 0.4 |
| | 12 | 24.2 | 0 | 0 | 1.1 |
| | 15 | 24.0 | 0 | 0 | 1.2 |
| | 18 | 20.7 | 0 | 0 | 1.1 |
| | 21 | 9.1 | 0 | 0 | 0.5 |
| | 24 | 12.2 | 0 | 0 | 0.4 |
| Ni/Cu/K-Morden/S | 3 | 12.6 | 0 | 0 | |
| | 9 | 12.7 | 0 | 0 | |
| | 15 | 10.0 | 0 | 0 | |
| | 21 | 10.9 | 0 | 0 | |
| | 24 | 9.9 | 0 | 0 | |

*Nominal loading; actual may be much lower.

Under continuously sulfiding conditions, for example, if 2 ppm $H_2S$ were cofed along with hydrogen and alkane over this catalyst, or by use of our preferred sulfiding procedure, these catalysts would have longer on-stream times, higher selectivity, and more stable yield behavior, as shown in later examples.

CATALYSTS SULFIDED WITH CARBONACEOUS SULFUR COMPOUNDS

In one embodiment of the invention, nickel and nickel-chromium dehydrogenation catalysts are sulfided with particular reagents such as dimethylsulfoxide to obtain catalysts useful in the processes described in this application, and also in other known dehydrogenation processes.

The following examples illustrate this embodiment of the invention:

Each of the catalysts prepared as described in Examples 15 through 18 was sulfided using dimethylsulfoxide as sulfiding agent as described following Example 18.

Catalysts were life tested in ½" O. D. isothermal packed bed continuous reactor (17 ml catalyst) equipped with internal thermocouple, a preheater/mixer chamber, and product collection facilities. Hydrogen was fed through a mass flow controller and iso or normal butane through a liquid metering pump followed by a back-pressure valve into the thermostatted preheater/mixing chamber. This chamber was a 11 stainless steel vessel which had been packed with borosilicate glass rings and electrically heated. Mixed gases were then passed to the catalyst bed at high temperature. The effluent from the reactor which was housed in a clam-shell electrical heater, was passed through a back-pressure regulator, through a liquid trap, a wet test meter, and through a gas sampling bomb to vent. Periodic samples were analyzed by gas chromatography and mass spectrometry. Post-mortem analysis was conducted on aged catalysts.

EXAMPLE 14

A 4% Ni/3.5%Cs/$Al_2O_3$/S catalyst was prepared as follows: Gamma alumina granules (110 ml), 18/35 mesh) were dried at 130°/2 hours then calcined in a programmable furnace at 4° C./minute to 677° C., held at 670° C. for 1.5 hours, then heated at 4°/minute to 1080° and held for 2 hours. Nickel nitrate hexahydrate (11.67 g) was dissolved in dry acetone (26 ml) of sufficient quantity to bring the solid alumina to incipient wetness (0.42 ml/g). After impregnation, the solvent was weathered off, the solid charged to a tube furnace and heated in flowing hydrogen to 450° C. for 1 hour and cooled under nitrogen. Cesium nitrate (3.29 g) was dissolved in deionized water to give 28 ml of solution. This was used to impregnate the solid to incipient wetness. The solid was then dried in air at 130°, heated in flowing hydrogen to 450°, and held at 450° for 1 hour. The sample was stored under $N_2$ until used.

EXAMPLE 15

A 3.3% Ni/2% Cr/$SiO_2$ catalyst was prepared as follows: Silica gel PQ-1231G of 18/35 mesh (186 g) was dried at 120° C. overnight. This was impregnated to incipient wetness with an aqueous solution (208 ml) containing $Cr_2O_3$ (7.86 g) and dried at 120° C. overnight. The dried sample was then calcined in an ebullating bed under flowing air at 540° C. for 45 minutes, then cooled to 125° C. and held for 50 hours. After cooling, the solid was again impregnated to incipient wetness with an aqueous solution (208 ml) containing Ni($NO_3$)$_2$.6$H_2O$ (33.4 g) followed by drying at 120° C. A portion of the solid was then calcined in air at 540° C./2 hours, flushed with nitrogen, then reduced in flowing hydrogen at 450° C./2 hours, cooled under $H_2$, and then stored under $N_2$ until use. ICP chemical analysis indicated 3.3% Ni, 2.0% Cr (VF basis ).

EXAMPLE 16

A 3.4% Ni/3.4% Cr/4X Ba-L catalyst was prepared as follows:

Commercial zeolite L extrudate (Union Carbide lot 11842-31) was ground and sieved to give 103 g of 18/35 solid. An aqueous solution (500 ml) containing 12.2 g of $BaCl_2.2H_2O$ was used to ion exchange the zeolite as a stirred slurry at 80° C./30 minutes. A second exchange was then performed with a more concentrated solution (500 ml) containing barium chloride dihydrate (30.1 g) for 30 minutes followed by distilled water washing (3X, 500 ml) and drying at 115° C. overnight. The sample was then placed in a programmable muffle furnace and heated at 9° C./minute to 594° C. and held isothermally for 2 hours followed by cooling. The sample was then re-exchanged with two batches of aqueous solution (500 ml) containing 30.4 g barium chloride dihydrate per batch followed by washing and calcining as per above description. The sequence of ion exchange followed by calcination was repeated two additional times. Chemical analysis by ICP indicated 8.4% Ba, 2.7% K, and 0.033% Na. Powder x-ray diffraction indicated highly crystalline materials of the characteristic spectrum for zeolite L.

$Ba^{2+}L$ (40 ml) prepared as above was dried at 130° C. for one hour (3.4 g dry weight). Chromium trioxide (2.82 g) aqueous solution (18 ml) was used to impregnate the zeolite to incipient wetness. After drying at 130° C., the solid was heated in flowing air in a tube furnace held at 540° C. for 1 hour and cooled. The solid was then impregnated to incipient wetness with an acetone solution (18 ml) of $Ni(NO_3)_2.5H_2O$ (7.5 g). After the solvent had been evaporated in an air draft, the sample was reduced in flowing hydrogen at 450° C./2 hours, and stored under nitrogen until used. Chemical analysis by ICP indicated 3.4% Cr and 3.4% Ni.

EXAMPLE 17

A catalyst was prepared as follows:

This sample was prepared by following a variant of the procedure used to prepare the catalyst of example 16. After exchange of the zeolite as described therein, the zeolite was first impregnated with chromium followed by nickel impregnation using a similar procedure as above except heat. The sample was dried in a vacuum oven only after each impregnation. After drying of the fully impregnated zeolite at 120° C., the solid was charged to a tube furnace and heated in flowing air at 400° C./2 hours, cooled to room temperature under $N_2$, then N immediately sulfided in a flow of 5% $H_2S/H_2$ with gradual heating to 400° C. where the solid was held for 30 minutes. The sample was then cooled and stored under nitrogen until use.

EXAMPLE 18

A 3.5% Ni/3.5% Cr/$ZnAl_2O_4$ catalyst was prepared as follows:

A sample of zinc aluminate was ground and sieved to 18/35 mesh and calcined at 1500° F. for 1 hour. Chromium trioxide aqueous solution (4.02 g dissolved into 20 ml) was used to impregnate the zinc aluminate to incipient wetness. After oven drying at 300° C. overnight, the solid was impregnated with 20 ml of an acetone solution of 9.96% nickel nitrate hexahydrate to incipient wetness. After evaporating the solid in an air draft and drying further at 230° C. under vacuum, the solid was treated in a flow of 4% $H_2$ in $N_2$ while slowly raising the temperature to 400° C. At 400° C., gas flow was switched to 100% $H_2$ and heating continued for 1 hour followed by treatment with 5% $H_2S/H_2$ for 0.5 hour at 400° C. After cooling, the sample was stored under $N_2$ until use. ICP analysis indicated 3.5% Ni, 3.5% Cr.

Sulfiding was conducted by injection of measured quantities of dimethylsulfoxide (DMSO) into the preheater section of the reactor after catalyst loading under flowing hydrogen. Temperature was ramped from 400° C. to 550° C. over a three hour period, followed by additional hydrogen flow for 3 to 10 hours at 550° to 600° C. prior to commencement of each run.

Hydrogen sulfide at levels between 2 to 200 ppm was sometimes continuously fed along with hydrogen throughout each run. The higher levels of $H_2S$ resulted in poor performance. Typical S/Ni ratios used for sulfiding with DMSO were 2-10.

All catalysts used were 18-35 mesh and some had been pre-reduced and briefly sulfided with $H_2$ followed by passivation with 2% $O_2$ in $N_2$, to enable handling in room air while loading each reactor.

Occasional regeneration was performed by purging the system with nitrogen followed by introduction of air at 400°-510° C. for periods of 3-8 hours. After another nitrogen purge, hydrogen was introduced to re-reduce the catalyst followed by resulfiding with DMSO and further hydrogen treatment. Time required for regeneration or sulfiding was not counted as on stream time.

Test results from life testing are shown in Table IV for Ni or Ni+Cr catalysts on several supports. Each of the catalysts was sulfided in-situ with DMSO. Various ratios of $H_2$ to butane were used; no butadiene was detected during these runs. In some runs, partial regeneration was conducted after the catalyst had deactivated. No attempt was made to completely regenerate; had regenerations been conducted longer, all catalysts would probably have returned to their initial activities.

TABLE IV

Comparison of catalyst performance for iso-butane dehydrogenation in packed bed reactor Example 14:
GHSV = 900 h$^{-1}$, $H_2/iC_4H_{10}$ = 1.1-1.4, T = 600° C.
4% Ni/3.5% Cs/$\gamma$ $Al_2O_3$/S

| Time On-Stream (Hours) | Mole % Conversion | Carbon Selectivity To: | |
|---|---|---|---|
| | | $C_4$= | $C_4$= + $C_3$= |
| 2 | 18.3 | 89.6 | 92.1 |
| 19 | 14.8 | 92.1 | 94.4 |
| 22 | 15.1 | 91.0 | 93.2 |
| 45 | 14.9 | 94.9 | 97.3 |
| 48 | 15.4 | 91.8 | 94.1 |
| 80 | 11.5 | 91.3 | 94.2 |
| 98 | 13.4 | 87.7 | 90.4 |

Example 15:
GHSV = 570 h$^{-1}$, $H_2/nc_4H_{10}$ = 5.5, T = 597 ± 2° C.
3.3% Ni/2% Cr/$SiO_2$/S

| Time | Conversion | Sel. $C_4$= |
|---|---|---|
| 54 | 41.2 | 27.3 |
| 57 | 18.4 | 76.1 |
| 60.5 | 17.9 | 74.2 |
| 80 | 15.6 | 74.0 |
| 104 | 13.5 | 74.0 |
| 153 | 12.2 | 75.5 |
| 183 | 11.0 | 74.0 |
| 238 | 9.7 | 74.8 |
| 262 | 9.1 | 74.8 |

Example 16: (Par. 1)
GHSV = 650 h$^{-1}$, T = 602 ± 2° C., 3.4% Ni/3.4% Cr/4X XC Ba-L/S, $H_2/iC_4H_{10}$ = 6

TABLE IV-continued

Comparison of catalyst performance for iso-butane dehydrogenation in packed bed reactor

| Time | Conversion | Selectivity $C_4=$ |
|---|---|---|
| 2 | 36.6 | 75.1 |
| 4 | 34.3 | 81.0 |
| 6 | 33.5 | 81.6 |
| 27 | 30.0 | 83.4 |
| 50 | 27.9 | 81.1 |
| 65 | 22.2 | 78.8 |
| 128 | 22.2 | 84.4 |
| 155 | 20.8 | 86.0 |
| 200 | 20.0 | 84.0 |
| 223 | 18.4 | 84.8 |
| Partial Air Regeneration & DMSO $H_2/iC_4 = 3$ | | |
| 230.5 | 35.6 | 78.5 |
| 251 | 29.8 | 81.3 |
| 255 | 26.1 | 85.4 |
| 275 | 23.8 | 85.4 |
| 297 | 21.4 | 85.7 |
| 330 | 15.6 | 86.3 |
| $H_2$ Treatment | | |
| 358 | 20.4 | 84.7 |

Example No. 16: (Par. 2)
GHSV = 650 h$^{-1}$, T = 602 ± 2° C., 4% Ni/4% Cr/4X XC Ba-L/S, $H_2/iC_4 = 3.5 \pm 0.5$

| Time | Conversion | Selectivity To $C_4=$ |
|---|---|---|
| 6 | 36.2 | 81.3 |
| 26 | 30.4 | 82.3 |
| 50 | 30.0 | 84.3 |
| 77 | 23.6 | 84.2 |
| 84 | 24.2 | 84.8 |
| 108 | 22.6 | 84.7 |
| 132 | 20.2 | 84.7 |
| 155 | 20.0 | 84.5 |
| 164 | 18.3 | 84.5 |
| 184 | 15.7 | 85.4 |
| 209 | 14.9 | 86.0 |
| 214 | 15.0 | 87.2 |
| 241 | 13.4 | 87.0 |
| 258 | 13.0 | 87.0 |
| Partial Air Regen. & DMSO Sulfiding 10 ppm $H_2S$ Co-Feed | | |
| 265 | 26.7 | 85.6 |
| 275 | 24.6 | 87.0 |
| 284 | 24.2 | 84.4 |
| 304 | 22.4 | 84.6 |
| 327 | 20.0 | 84.8 |
| 358 | 17.3 | 85.8 |
| 410 | 15.7 | 86.1 |
| 430 | 13.9 | 86.7 |

Example No. 17:
GHSV = 912 h$^{-1}$, $H_2/iC_4$ = 1.9, T = 602 ± 1° C. 4% Ni/4% Cr/4X XC Ba-L/S

| Time On-Stream | Conversion | Carbon Molar Selectivities | |
|---|---|---|---|
| | | $C_4=$ | $C_4= + C_3=$ |
| 1 | 22.1 | 87.5 | 91.5 |
| 2 | 20.0 | 87.5 | 91.7 |
| 8 | 16.2 | 88.7 | 93.1 |
| 11 | 15.1 | 88.7 | 93.1 |
| 27 | 12.8 | 88.9 | 93.5 |
| 31 | 12.6 | 87.1 | 91.6 |
| 51 | 10.9 | 87.0 | 91.5 |
| 52 | 10.5 | 91.6 | 96.3 |

Example 18:
GHSV = 950 h$^{-1}$, $H_2/iC_4$ = 1.9, T = 599° C., 3.5%

| Time On-Stream | Conversion | Carbon Molar Selectivities | |
|---|---|---|---|
| | | $C_4=$ | $C_4= + C_3=$ |
| Ni/3.5% Cr/ZnAl$_2$O$_4$/H$_2$S | | | |
| 2 | 39.4 | 76.1 | 84.5 |
| 6 | 27.9 | 80.2 | 89.8 |
| 28 | 26.1 | 65.9 | 74.8 |
| 32 | 15.1 | 67.7 | 75.4 |
| 37 | 11.5 | 80.2 | 88.8 |

The data in Table IV show that these catalysts have good selectivity characteristics and are long lived. They may be regenerated. Comparison of these data to data on similar catalysts sulfided with H$_2$S makes it evident that the catalysts described here which had been sulfided with DMSO demonstrated higher selectivities and longer on stream lives than those sulfided with only H$_2$S. Deactivation of the present catalysts is characterized by loss of activity rather than by loss of selectivity (probably due to loss of S) which was seen when only H$_2$S had been used as the sulfiding agent previously.

EXAMPLE 19

This example illustrates a method to modify the pore structure of the catalyst support. 110 grams of gamma alumina (ALCOA CS-105) were treated for 2 hrs at 80°-90° C. in a 1.8M aqueous solution of oxalic acid, then washed with hot distilled water and filtered. The solid was then calcined for 2 hrs in air at 910° C. The porosity in the range 10 to 50 angstroms was drastically reduced while that in the range 50 to 200 angstroms was significantly increased. In this particular case, the pore volume in the range 10 to 50 angstroms dropped from 0.16 ml/g in the commercial alumina to 0.06 ml/g in the treated sample. On the other hand, the pore volume in the range 50 to 200 angstrom increased from 0.30 to 0.40 ml/g.

A preferred method to reduce acidity of alumina catalyst supports is the incorporation of cesium as described in Example 20:

EXAMPLE 20

110 ml of gamma alumina (United Catalysts CS331-4, 225 m$_2$/g) 18/35 mesh were calcined in air for 1.5 hours at 1080° C. Then, the cesium was added by incipient wetness of 3.29 g of cesium nitrate dissolved in 28 ml of deionized water and subsequently dried in an oven at 130° C.

EXAMPLE 21

20 grams of gamma alumina (United Catalysts CS331-9) 18/35 mesh, precalcined at 980° C. for 10 hours, were impregnated with an aqueous solution of cesium nitrate (2.18 g. in 13 ml). After drying at 130° C. for 2½ hours, the sample was further impregnated with a solution of nickel nitrate in acetone (6.25 g of Ni(NO$_3$)$_2$. 6H$_2$O in 20 ml). The sample was dried in air at 180° C. and subsequently treated with NH$_4$OH. This base treatment was done by spraying the liquid over the catalyst using a liquid/solid ratio of about 0.6 ml/g. The sample was reduced in steps (100° C./30 min. under H$_2$, kept at 600° C. for 2 hours, sulfide with DM80 (0.07 ml/gr. wt.), cooled in H$_2$ overnight, passivated in 4% O$_2$/N$_2$ and stored.

Table V shows the improvement of nickel-cesium-alumina catalysts in selectivity towards isobutane dehydrogenation achieved as a result of a decrease in isomerization activity. The data in Table V show that this decrease can be either effected by addition of an extra amount of cesium or by a calcination treatment before the loading of cesium. The catalyst containing 3% Cs without a pre-calcination treatment exhibited a relatively high isomerization activity and poor selectivity. By contrast, the other two catalysts in Table V, the one with 7% cesium and the pre-calcined one with a 3% cesium, exhibited high selectivities and no isomerization activity.

TABLE V

EFFECT OF ACIDITY ON SELECTIVITY

| CATALYST | SELECTIVITY % | | |
|---|---|---|---|
| | dehydrogenation | isomerization | hydrogenolysis |
| 8% Ni 3% Cs on $Al_2O_3$ | 75 | 20 | 5 |
| 8% Ni 7% Cs on $Al_2O_3$ | 87 | 0 | 13 |
| 3% Ni 3% Cs on pre-calcined $Al_2O_3$ | 89 | 0 | 10 |

Figure 8:
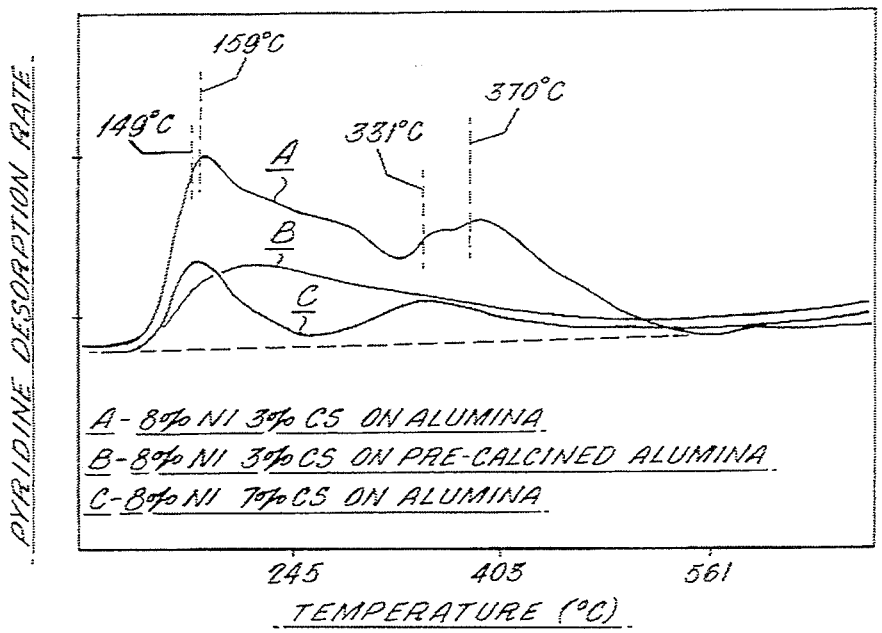
FIG. 8 shows the ammonia temperature programmed desorption peak areas as a function of temperatures for the following catalysts: (a) 8% Ni and 3% Cs on $Al_2O_3$, (b) 8% Ni and 7% Cs on $Al_2O_3$ and (c) 3% Ni and 3% Cs on pre-calcined $Al_2O_3$.

FIG. 8 of the drawings shows the reduction in TPD peak areas of pyridine desorption rate for the three catalysts whose selectivity data are shown in Table V. The sizes of the peaks observed between 130 and 500 C. are a measure of the degree of support acidity. It can be clearly seen that either the addition of extra amounts of cesium or the pre-calcination before the loading of cesium diminishes the support acidity.

The following examples illustrate the catalytic performance of the preferred catalysts of this invention as compared to other, known dehydrogenation catalysts:

EXAMPLE 22

25 g. of zinc aluminate, 20/40 mesh, were impregnated with 0.26 g of chloroplatinic acid and 0.11 g. of stannous chloride dihydrate dissolved in 9 ml of distilled water. The sample was dried overnight in an oven at 110° C. Then it was calcined at 300° C. for 1 hour, re-sieved, and stored.

EXAMPLE 23

32 g. of gamma alumina (Alcoa S-100), pre-calcined at 950° C. for 2 hours, were impregnated with 57 ml of a 2.1M KOH solution. After drying at 140° C., the sample was sequentially impregnated with $Pt(NH_3)_4Cl_2$ and $SnCl_2$ aqueous solutions, and calcined to yield a sample containing 0.39 weight percent Pt. and 0.39 weight percent Sn.

Figure 9:
FIG. 9 is an electron microscopic image of a catalyst containing 8% Ni and 7% Cs on alumina and containing, after use as a dehydrogenation catalyst 34.9% carbon.
Figure 11:
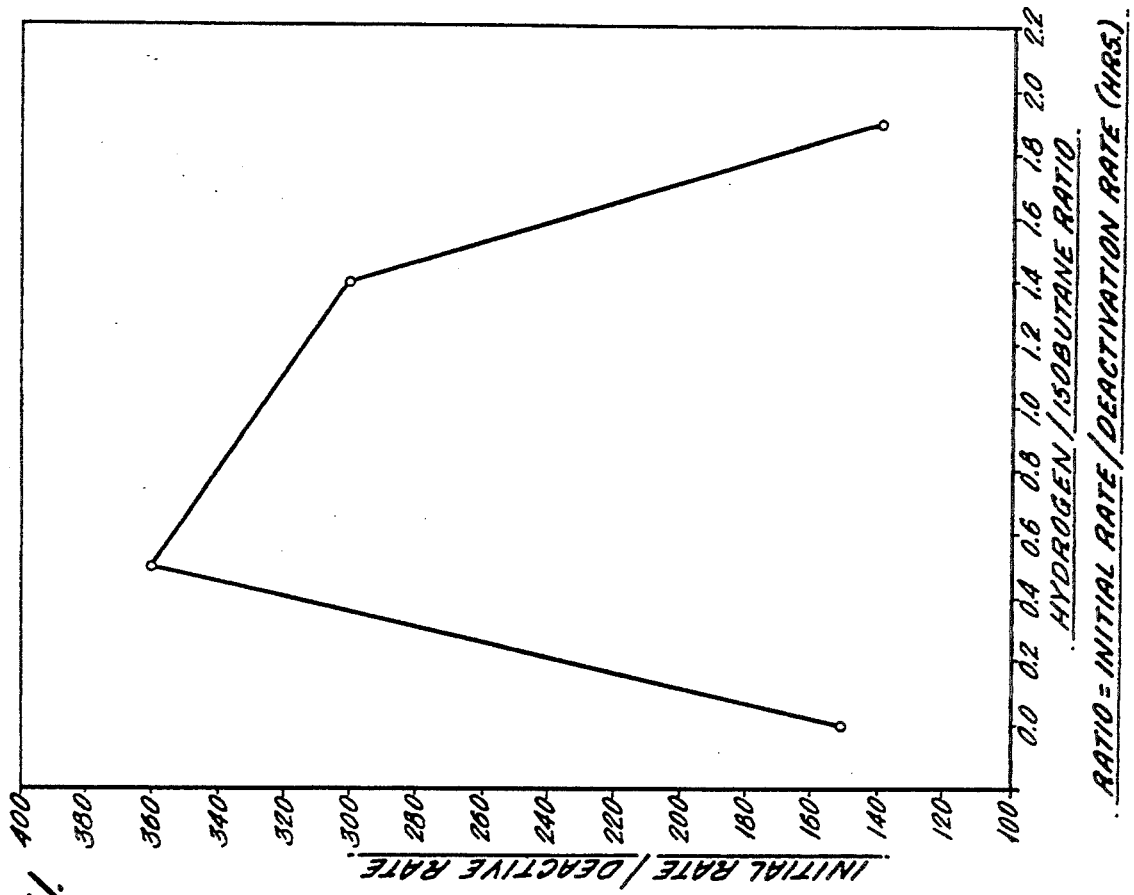
FIG. 11 shows the ratio of initial reaction rate to deactivation rate as a function of hydrogen/isobutane ratio.

The iso-butane dehydrogenation rates over the catalyst of Examples 21, 22 and 23, are given in FIG. 9 as a function of time on stream. These rates were obtained in a packed bed reactor, operating at 600° C., 15 PSIA, with LHSV of 1 to 1.5 and an $H_2$ to iso-butane ratio between 1.0 and 2.0. It is demonstrated that the preferred catalyst of Example 21 is superior to the Pt-based catalysts of Examples 22 and 23 in terms of activity and stability.

EXAMPLE 24

This example illustrates the use of a temporary pore filling reagent to achieve preferential deposition of the nickel catalyst component in the larger pore region.

39.60 grams of gamma alumina (Alcoa CSS-105) ground and sieved to 18/35 mesh were calcined in air at 950° C. for 2 hrs. The alumina was then impregnated with 8.00 cc of ethylene glycol at room temperature and placed in an oven at 197° C. for 5 min. The amount of ethylene glycol remaining in the catalysts was found to be 5.35 g, which corresponds to about 0.125 ml/g catalyst. Due to capillary effects, the condensation of ethylene glycol at its normal boiling point should occur in the smaller pores. The subsequent incorporation of nickel was done by incipient wetness impregnation of 11.92 grams of nickel nitrate $(Ni(NO_3)_2.6H_2O)$ dissolved in 24 ml of acetone. The impregnated sample was then dried in air at 140° C. for 25 min and then calcined at 500° C. for 2 hrs. Finally, to reduce the acidity of the support, cesium was incorporated by incipient wetness of 1.84 grams of cesium nitrate dissolved in 24 ml of distilled water. Then, it was dried in air at 100° C. for 8 hrs and calcined at 550° C. for 2 hrs.

EXAMPLE 25

This example illustrates the deliberate preformation of a barrier layer by repeated impregnation-calcination steps such that the first calcination is above 500° C. in oxygen or air, followed by one or more subsequent impregnation-low temperature calcination steps. This layer hinders or prevents the formation of nickel aluminate during calcination or catalyst regeneration at high temperatures.

38.25 grams of gamma-alumina (Alcoa CSS-105), 18/35 mesh, were impregnated with 2.50 g of $Ni(NO_3)_2.6H_2O$ dissolved in 28 ml of acetone. The sample was subsequently dried in an oven at 250° C. for 1 hr and then calcined in air at 500° C. for 1 hr and at 950° C. for 2 hrs. After this treatment, the color of the sample was a light bluish green. The second addition of nickel was also performed by incipient wetness impregnation using 12.58 g of nickel nitrate dissolved in 29 ml of acetone. This time, the sample was dried at 100° C. for 1 hr and mildly calcined at 200° C. for 2 hrs. The final step was the addition of cesium, following the procedure explained above for other samples.

EXAMPLE 26

2.0 grams of alumina (United Catalysts CS 331-4), precalcined at 100° C. for 10 hours were impregnated with an aqueous solution of 0.36M (Cu(II) acetate using a liquid/solid ratio of 0.6 $cm^3$/g., resulting in a copper loading of 1.38 weight percent. After drying in air, the sample was calcined at 600° C. for 1 hour. Subsequently, it was impregnated with Ni nitrate in acetone using a liquid/solid ratio of 1.0 $Cm^3$/g. to yield a nickel loading of 3.7 weight percent.

The sample was then dried at 130° C., and reduced in $H_2$ at 600° C. The temperature programmed reduction profiles in FIG. 10 illustrate the effect of the barrier layer on the reducibility of nickel on the catalysts of examples 21 and 27.

Increasing the calcination temperature makes it more difficult to reduce the nickel, but when a Cu barrier layer is present, this effect is greatly reduced. In this case, a large fraction of Ni can still be reduced even after calcination at 600° C.

EXAMPLE 27

A catalyst prepared according to Example 28 was tested for selective hydrogen combustion as described in Example 28 but with a different feed composition and gas hourly space velocity. Feed composition was 18.25 mol % $CH_4$, 4.14 mol % $H_2$, 62.78 mol % isobutylene, 4.28% $O_2$. Reactor pressure was 110±10 psig during the runs. The results are tabulated below:

| T (°C.) | GHSV ($h^{-1}$) | $H_2$ Conversion | $O_2$ Conv. | R | Oxygen Atom Selectivity to Water |
|---|---|---|---|---|---|
| 549 | 18323 | 85.4 | 96.2 | 5.3 | 76.8 |
| 537 | " | 88.5 | 91.0 | 4.3 | 72.7 |
| 571 | " | 79.1 | 94.6 | 4.0 | 70.6 |
| 569 | " | 81.4 | 87.3 | 3.1 | 64.7 |

-continued

| T (°C.) | GHSV (h⁻¹) | H₂ Conversion | O₂ Conv. | R | Oxygen Atom Selectivity to Water |
|---|---|---|---|---|---|
| 458 | " | 54.8 | 32.5 | 6.3 | 78 |
| 453 | " | 75.3 | 27.8 | 5.5 | 75 |
| 485 | 9162 | 87.8 | 99.7 | 5.3 | 76.5 |
| 497 | " | 92 | 99.8 | 4.4 | 72.7 |
| 538 | " | 92 | 99.7 | 4.5 | 73.4 |

Oxygen atom selectivity to water is defined as:

$$\frac{[H_2O]}{[H_2O] + [CO] + 2[CO_2]} \times 100$$

in the product stream.

EXAMPLE 28

This example illustrates preparation and testing of catalysts for the selective combustion of hydrogen.

Catalysts for selective hydrogen combustion were prepared then tested in a steady state continuous reactor system.

Stannic chloride pentahydrate (38 g.) was dissolved into 75 ml of distilled water. Phosphoric acid (85%, 9.5 g.) was dissolved into 40 ml of distilled water. These solutions were combined as solution A. Ammonium hydroxide (concentrated, 35 ml) was diluted with 200 ml distilled water. The resulting solution was labeled B. The two solutions, A and B, were alternatively added to a beaker containing 50 ml of distilled water stirred with a magnetic stirrer and fitted with pH electrodes. pH was maintained in the range 3-4 until the entire amounts of A and B had been added. The resulting white precipitate was collected by filtration, washed with distilled water 3 times, and dried at 125° C. overnight in air. The solid was then ground and sieved to 18/35 mesh.

A feedstock composed as follows was used to simulate product from dehydrogenation processes as disclosed herein and was passed over the catalyst at steady state conditions at various temperatures in a packed bed reactor. On-line analysis of products enabled relative catalyst performance to be gauged:

| Mol. % Feed Composition | |
|---|---|
| H₂ | 11.07 |
| O₂ | 5.05 |
| N₂ | 19.65 |
| H₂O | 0.269 |
| CH₄ | 30.66 |
| iC₄H₁₀ | 0.054 |
| iC₄H₈ | 33.23 |

Total GHSV was about 30,000 h-1 in these tests. On stream times of several hours at each temperature were achieved. A selectivity term, R, was defined:

$$R = \frac{[H_2O]}{[CO] + [CO_2]}$$

where $H_2O$, $CO$, $CO_2$ refer to those components in the product gas stream.

Given the feed composition, completely random combustion of any combustible feed components that impinged on the surface would result in an R value of 1.3. R values above about 2 indicate some degree of preferential combustion of hydrogen rather than of either methane or isobutylene. Acceptable in th screening test catalysts have R values above about 4 at ≧95% O₂ conversion.

Catalysts were tested at various temperatures between 300°-600° C., but only high temperature data are reported here since these reflect the most useful temperature range of the process.

Table VI lists comparative data for various compositions including those of the present invention. R values were determined by product analysis in which the molar composition of each component was measured by a multidimensional GC technique.

Table VI shows the results obtained with catalyst according to this embodiment of the invention, number 6, catalyst prepared according to Example 1 of U.S. Pat. No. 4,788,371, number 5, and other catalysts showing substantially lesser degrees of activity for the selective oxidation process, numbers 1 through 4. Comparison of catalysts 5 and 6 shows higher selectivities for the catalyst according to the invention, number 6, at the high temperatures, 560° C. and above.

TABLE VI

COMPARISON OF CATALYSTS FOR HYDROGEN COMBUSTION AT STEADY STATE
(2-4 HOURS ON STREAM; GHSV~30,000 h⁻¹)

| | CATALYST | T (°C.) | R |
|---|---|---|---|
| 1. | Cu²⁺ Exchanged Zeolite 3A | 549 | 2.1 |
| | Diluted 1:1 with αAl₂O₃ | 549 | 1.9 |
| 2. | Cr³⁺ Exchanged Zeolite 3A | 442 | 1.4 |
| | Diluted 1:1 with αAl₂O₃ | 478 | 1.8 |
| | | 552 | 1.6 |
| 3 | α-Al₂O₃ | 565 | 2.0 |
| | | 561 | 2.0 |
| 4 | 4% Ni/3.5% Cs/Al₂O₃ | 459 | 1.6 |
| 5. | *Pt/Sn/Cs/Al₂O₃ Diluted | 563 | 3.5 |
| | 1.1 with αAl₂O₃ | 572 | 4.1 |
| | | 508 | 10.4 |
| | | 504 | 6.1 |
| 6. | SnPO₄ Gel | 560 | 4.3 |
| | | 574 | 5.1 |
| | | 466 | 4.9 |
| | | 449 | 5.0 |

*Catalyst prepared according to Example 1 of U.S. Pat. No. 4,788,371
+The invention

The invention claimed is:

1. A new composition of matter having catalytic activity for dehydrogenation of dehydrogenatable organic compounds which comprises reduced and sulfided nickel on siliceous supports which have been pretreated with chromium compounds and oxidized to provide surface-anchored chromyl species.

2. Composition according to claim 1 comprising nickel and tin on chromia-covered silica.

3. Composition of matter having catalytic activity for dehydrogenation of alkanes which comprises nickel supported on a non-acidic form of zeolite L wherein said nickel is sulfided.

4. Composition according to claim 3 wherein said nickel is alloyed with tin or indium.

5. Composition according to claim 3 wherein said nickel is supported on barium-exchanged L zeolite.

6. Process for preparation of dehydrogenation catalyst which comprises contacting a metal or metal compound having activity for dehydrogenating organic compounds with a carbonaceous sulfur compound under sulfiding conditions.

7. Catalyst prepared by the process of claim 6.

8. Process according to claim 6 wherein said sulfur compound is a dialkylsulfoxide.

9. Catalyst comprising a metal or metal compound having activity for dehydrogenating organic compounds on a porous alumina support in which pores having radius in the range from 20 to 50 Angstroms have pore volume less than 0.1 ml. per gram of said support, and pores having radius in the range from 50 to 200 Angstroms have pore volume in the range from 0.30 to 1.50 ml per gram of said support.

10. Catalyst according to claim 9 wherein said pores having radius in the range from 20 to 50 Angstroms have pore volume less than 0.05 ml per gram of said support and said pores having radius in the range from 50 to 200 Angstroms have pore volume in the range from 0.40 to 0.80 ml per gram of said support.

11. Process for preparation of dehydrogenation catalyst support which comprises leaching a porous solid metal oxide catalyst support with a liquid solution of carboxylic acid, and calcining the leached support.

12. Catalyst comprising a metal or metal compound having activity for dehydrogenating organic compounds on a porous support which has been leached with a carboxylic acid and calcined.

13. Catalyst according to claim 12 wherein said acid is succinic acid.

14. Catalyst according to claim 12 wherein said acid is oxalic acid.

15. Process for preparation of dehydrogenation catalyst comprising a metal or metal compound having activity for dehydrogenating organic compounds, and a Group III oxide or hydroxide support, in which reaction of said metal with said support is reduced by forming a layer of a Group IV metal oxide or hydroxide on said support prior to applying said metal or metal compound to said support.

16. Process according to claim 15 wherein said support is treated with an organozirconate or organotitanate, and dried and calcined to form said layer.

17. Catalyst prepared by the process of claim 15.

18. Process for preparation of dehydrogenation catalyst comprising a first metal or metal compound having activity for dehydrogenating organic compounds and a Group III oxide or hydroxide support, in which reaction of said metal with said support is reduced by reacting said support with a second metal or metal compound prior to applying said first metal to said support.

19. Process according to claim 18 wherein said first metal is nickel and said second metal is copper and copper aluminate is formed on the support prior to applying said first metal to said support.

20. Catalyst prepared by the process of claim 18.

21. Process for preparation of dehydrogenation catalyst which comprises contacting a porous support containing larger and smaller pores, with a liquid organic compound comprising polyhydric alcohol, optionally containing ether groups, under conditions at which said compound selectively enters or remains in said smaller pores of said support, contacting the resulting support with a liquid containing a compound of a metal having dehydrogenating activity to selectively deposit said metal compound in said larger pores of said support, and removing said organic compound from said smaller pores.

22. Process according to claim 21 wherein said support is contacted with said organic compound in liquid phase, then heated to selectively volatilize said organic compound from said larger pores.

23. Process according to claim 21 wherein said support is contacted with said organic compound in vapor phase, then cooled to selectively condense said organic compound in said smaller pores.

24. Catalyst prepared by the process of claim 21.

25. Process for preparation of a dehydrogenation catalyst which comprises impregnating a porous support with a metal or metal compound having activity for dehydrogenation of organic compounds, calcining said support at a first temperature sufficiently high to react said metal with said support, reimpregnating said support with the same or different metal or metal compound having said activity, and calcining said support at a second temperature lower than said first temperature.

26. Process according to claim 25 wherein said first temperature is in the range from 500° to 1000° C., and said second temperature is in the range from 200° to 600° C.

27. Process according to claim 25 wherein said metal is nickel and said support is alumina.

28. Catalyst prepared by the process of claim 25.

29. Process for preparing dehydrogenation catalyst which comprises forming a carbonaceous layer on a noncarbonaceous porous support, and then depositing a metal or metal compound having dehydrogenating activity upon said carbonaceous layer.

30. Catalyst prepared by the process of claim 29.

* * * * *